(12) United States Patent
Smith et al.

(10) Patent No.: US 10,779,872 B2
(45) Date of Patent: Sep. 22, 2020

(54) BONE ANCHOR INSERTION INSTRUMENTS AND METHODS

(71) Applicant: Medos International Sarl, Le Locle (CH)

(72) Inventors: Keanan Smith, Quincy, MA (US); Nicholas Pavento, North Attleboro, MA (US); John DiVincenzo, South Weymouth, MA (US)

(73) Assignee: Medos International Sarl, Le Locle (CH)

( * ) Notice: Subject to any disclaimer, the term of this patent is extended or adjusted under 35 U.S.C. 154(b) by 385 days.

(21) Appl. No.: 15/801,917

(22) Filed: Nov. 2, 2017

(65) Prior Publication Data

US 2019/0125421 A1    May 2, 2019

(51) Int. Cl.
| | |
|---|---|
| *A61B 17/88* | (2006.01) |
| *A61B 17/00* | (2006.01) |
| *A61B 17/70* | (2006.01) |
| *A61B 17/56* | (2006.01) |
| *A61B 17/16* | (2006.01) |
| *A61B 90/00* | (2016.01) |

(52) U.S. Cl.
CPC .......... *A61B 17/8875* (2013.01); *A61B 17/16* (2013.01); *A61B 17/7082* (2013.01); *A61B 2017/00407* (2013.01); *A61B 2017/00477* (2013.01); *A61B 2017/564* (2013.01); *A61B 2090/031* (2016.02); *A61B 2090/08021* (2016.02)

(58) Field of Classification Search
CPC ................................................ A61B 17/8875
USPC ....................................................... 606/104
See application file for complete search history.

(56) References Cited

U.S. PATENT DOCUMENTS

| | | | |
|---|---|---|---|
| 2,631,584 | A | 3/1953 | Purificato |
| 6,019,776 | A | 2/2000 | Preissman et al. |
| 6,402,757 | B1 | 6/2002 | Moore, III et al. |
| 6,736,820 | B2 | 5/2004 | Biedermann et al. |
| 6,827,722 | B1 | 12/2004 | Schoenefeld |

(Continued)

FOREIGN PATENT DOCUMENTS

| | | |
|---|---|---|
| CN | 1341402 A | 3/2002 |
| JP | H07163599 A | 6/1995 |
| WO | 2016022333 A1 | 2/2016 |

OTHER PUBLICATIONS

International Search Report and Written Opinion for PCT/US18/58716 dated Jan. 22, 2019 (14 pages).

*Primary Examiner* — Si Ming Ku
(74) *Attorney, Agent, or Firm* — Mintz Levin Cohn Ferris Glovsky and Popeo, P.C.

(57) ABSTRACT

Surgical instruments and methods for implanted bone anchor assemblies into bone are disclosed herein. In one exemplary embodiment, an instrument is provided having an anchor drive assembly and a stylet assembly. The anchor drive assembly can have a first handle and an elongate shaft having a distal tip configured to couple to a bone anchor assembly. The stylet assembly can have a second handle and a stylet extending through the elongate shaft. The instrument can have a disengaged position and an engaged position such that rotation of the first handle is effective to drive the bone anchor assembly into bone only when the instrument is in the engaged position, and rotation of the second handle is effective to cause axial translation of the stylet relative to the elongate shaft.

16 Claims, 15 Drawing Sheets

(56) References Cited

U.S. PATENT DOCUMENTS

| | | | |
|---|---|---|---|
| 6,974,460 | B2 | 12/2005 | Carbone et al. |
| 6,981,974 | B2 | 1/2006 | Berger |
| 7,179,261 | B2 | 2/2007 | Sicvol et al. |
| 7,207,995 | B1 | 4/2007 | Vandewalle |
| 7,338,494 | B2 | 3/2008 | Ryan |
| 7,488,323 | B2 | 2/2009 | Bacastow et al. |
| 7,604,643 | B2 | 10/2009 | Ciccone et al. |
| 7,892,207 | B2 | 2/2011 | Simonton et al. |
| 7,938,836 | B2 | 5/2011 | Ainsworth et al. |
| 8,192,466 | B2 | 6/2012 | Yue et al. |
| 8,216,243 | B2 | 7/2012 | Yevmenenko et al. |
| 8,236,006 | B2 | 8/2012 | Hamada |
| 8,282,651 | B2 | 10/2012 | Ciccone et al. |
| 8,303,601 | B2 | 11/2012 | Bandeira et al. |
| 8,372,076 | B2 | 2/2013 | Simonton et al. |
| 8,394,108 | B2 | 3/2013 | McLean et al. |
| 8,641,717 | B2 | 2/2014 | Defossez et al. |
| 8,715,293 | B2 | 5/2014 | Vandewalle |
| 8,777,954 | B2 * | 7/2014 | McLean ............ A61B 17/7032 606/86 A |
| 9,247,933 | B2 * | 2/2016 | Lanois ............ A61B 17/0401 |
| 9,289,249 | B2 | 3/2016 | Ramsay et al. |
| 9,855,087 | B2 | 1/2018 | Divincenzo et al. |
| 2005/0216027 | A1 | 9/2005 | Suh et al. |
| 2006/0079903 | A1 | 4/2006 | Wong |
| 2006/0129238 | A1 | 6/2006 | Paltzer |
| 2007/0016219 | A1 | 1/2007 | Levine |
| 2008/0147128 | A1 | 6/2008 | Fritzinger |
| 2009/0275994 | A1 | 11/2009 | Phan et al. |
| 2010/0114174 | A1 | 5/2010 | Jones et al. |
| 2010/0211115 | A1 * | 8/2010 | Tyber ............ A61B 17/863 606/305 |
| 2010/0241124 | A1 | 9/2010 | Housman et al. |
| 2011/0054537 | A1 | 3/2011 | Miller et al. |
| 2011/0288599 | A1 | 11/2011 | Michielli et al. |
| 2012/0203357 | A1 | 8/2012 | Bleicher et al. |
| 2012/0253355 | A1 | 10/2012 | Murray et al. |
| 2013/0012954 | A1 | 1/2013 | Paroth et al. |
| 2013/0053901 | A1 | 2/2013 | Cormier et al. |
| 2013/0096618 | A1 | 4/2013 | Chandanson et al. |
| 2013/0190825 | A1 * | 7/2013 | Perrow ............ A61B 17/8042 606/281 |
| 2013/0310842 | A1 | 11/2013 | Winkler et al. |
| 2014/0276892 | A1 | 9/2014 | Pakzaban et al. |
| 2014/0276894 | A1 | 9/2014 | Ramsay et al. |
| 2015/0196340 | A1 | 7/2015 | Combrowski |
| 2015/0201985 | A1 | 7/2015 | Rampersaud et al. |
| 2015/0201987 | A1 | 7/2015 | Lemoine et al. |
| 2016/0030100 | A1 * | 2/2016 | Divincenzo ........ A61B 17/7082 606/104 |
| 2016/0183995 | A1 | 6/2016 | Zrinski et al. |
| 2016/0296266 | A1 | 10/2016 | Chandanson et al. |
| 2017/0196601 | A1 | 7/2017 | Koenig et al. |
| 2018/0110553 | A1 | 4/2018 | DiVincenzo et al. |
| 2018/0132920 | A1 | 5/2018 | Vikinsky et al. |
| 2018/0368893 | A1 | 12/2018 | DiVincenzo et al. |
| 2020/0100817 | A1 | 4/2020 | DiVincenzo et al. |
| 2020/0100824 | A1 | 4/2020 | DiVincenzo et al. |

* cited by examiner

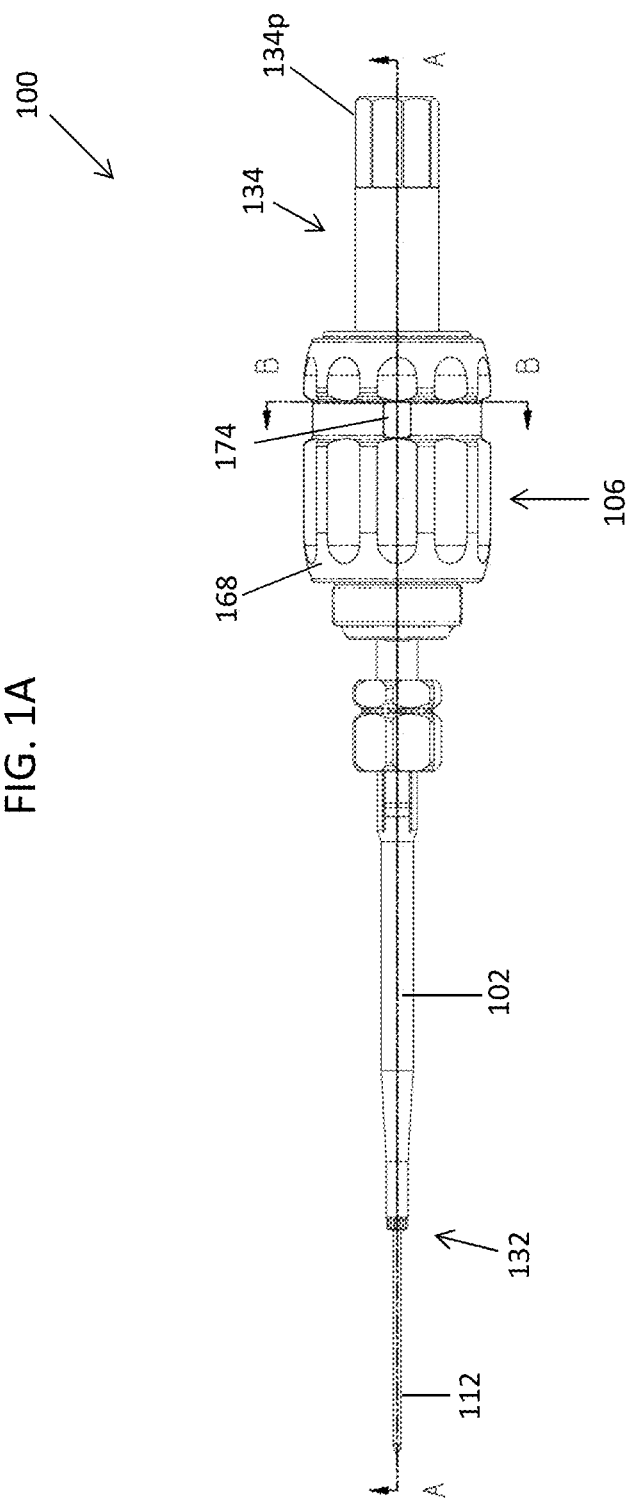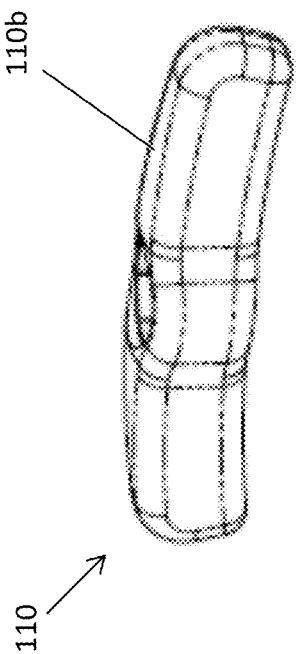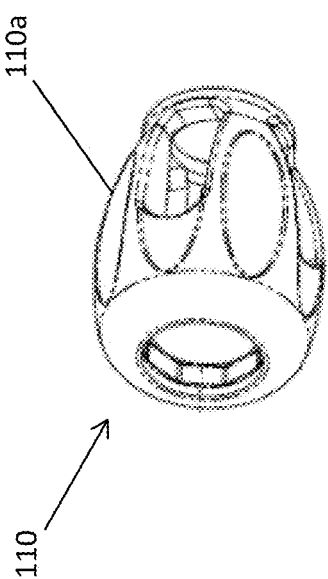
FIG. 1A
FIG. 1B
FIG. 1C

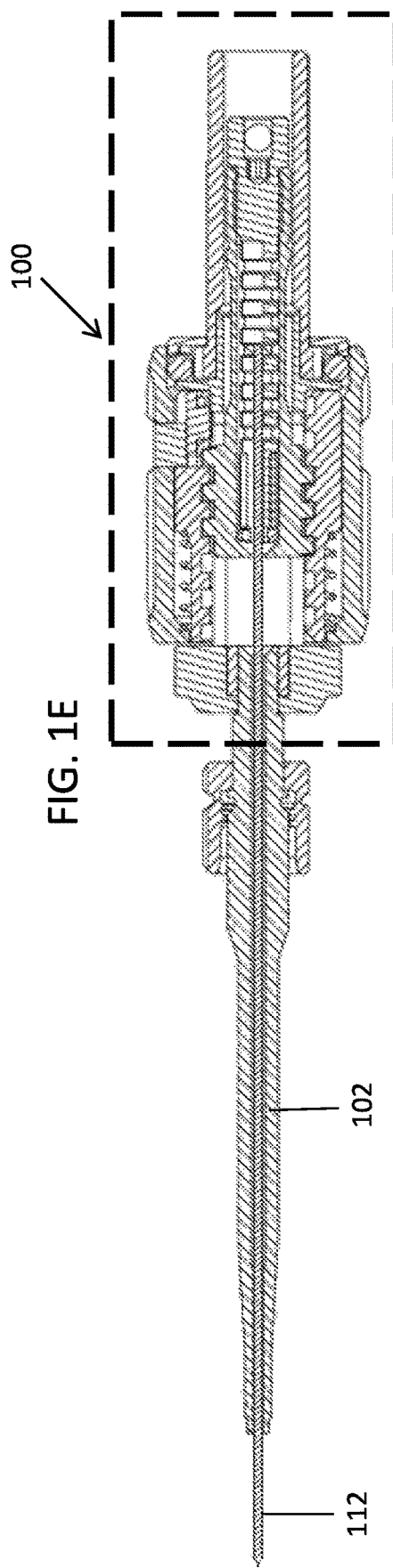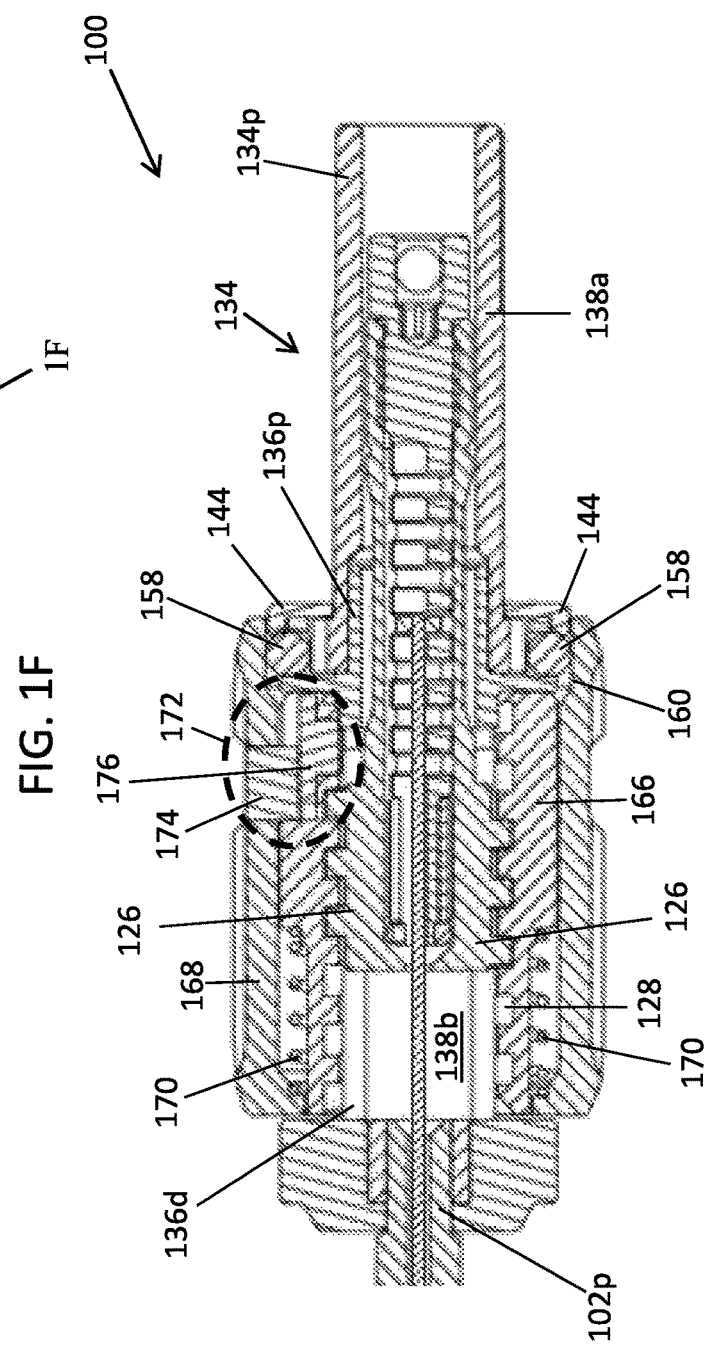

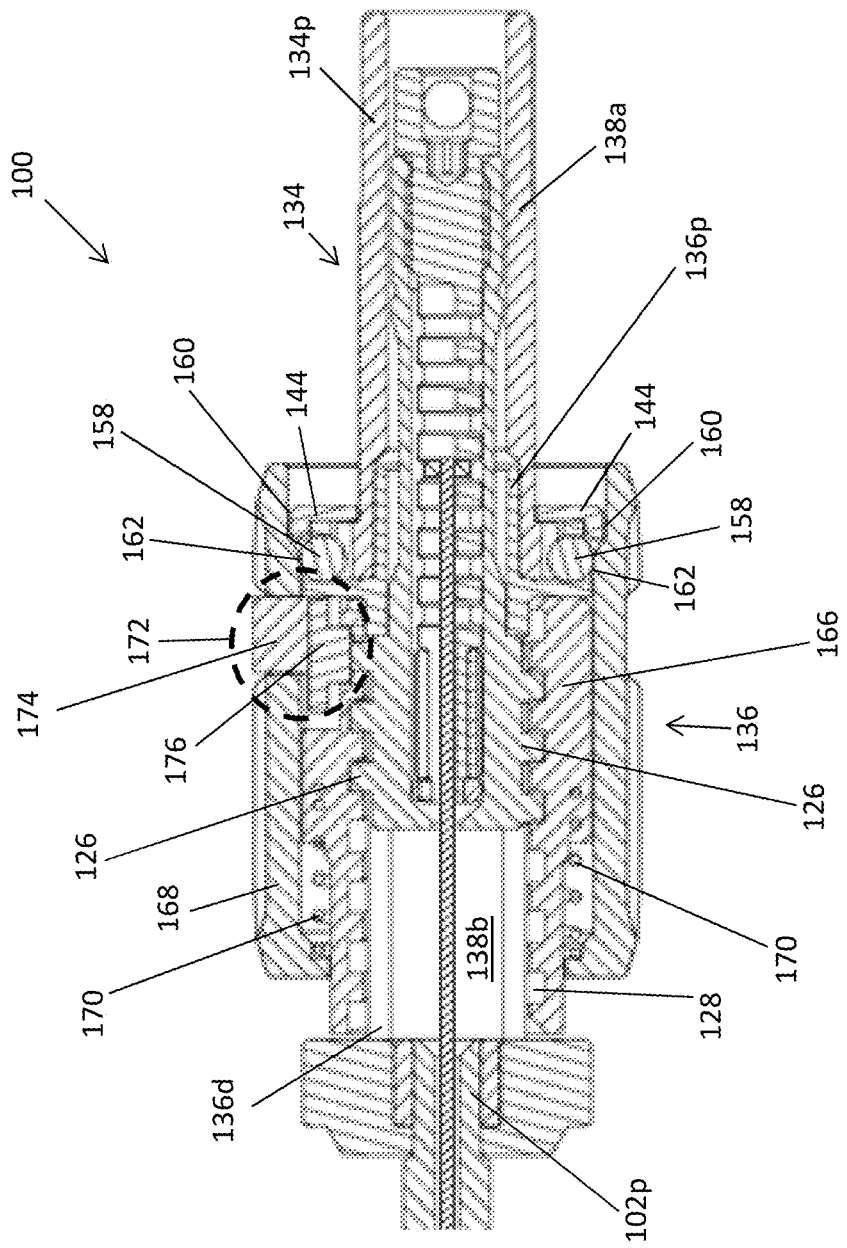

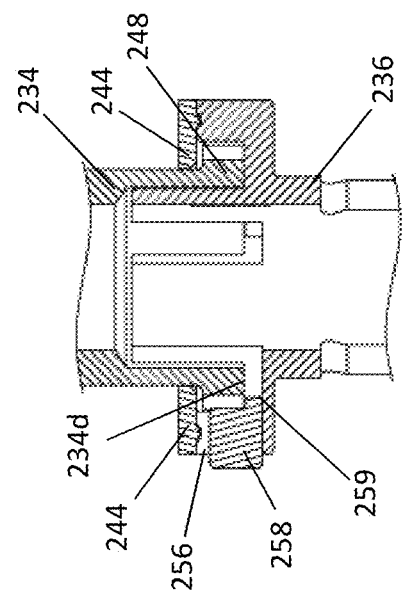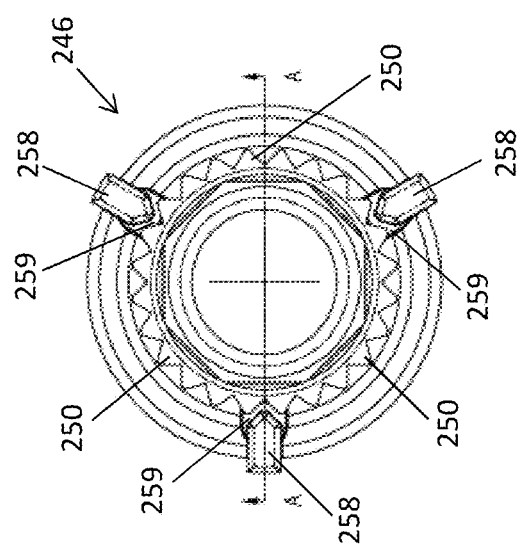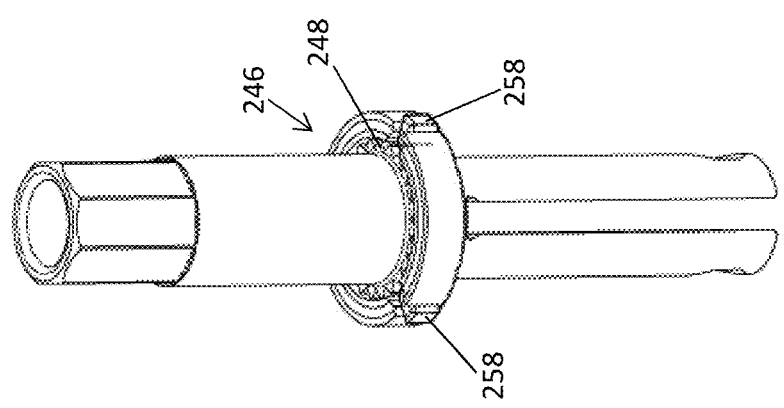
FIG. 4C
FIG. 4B
FIG. 4A

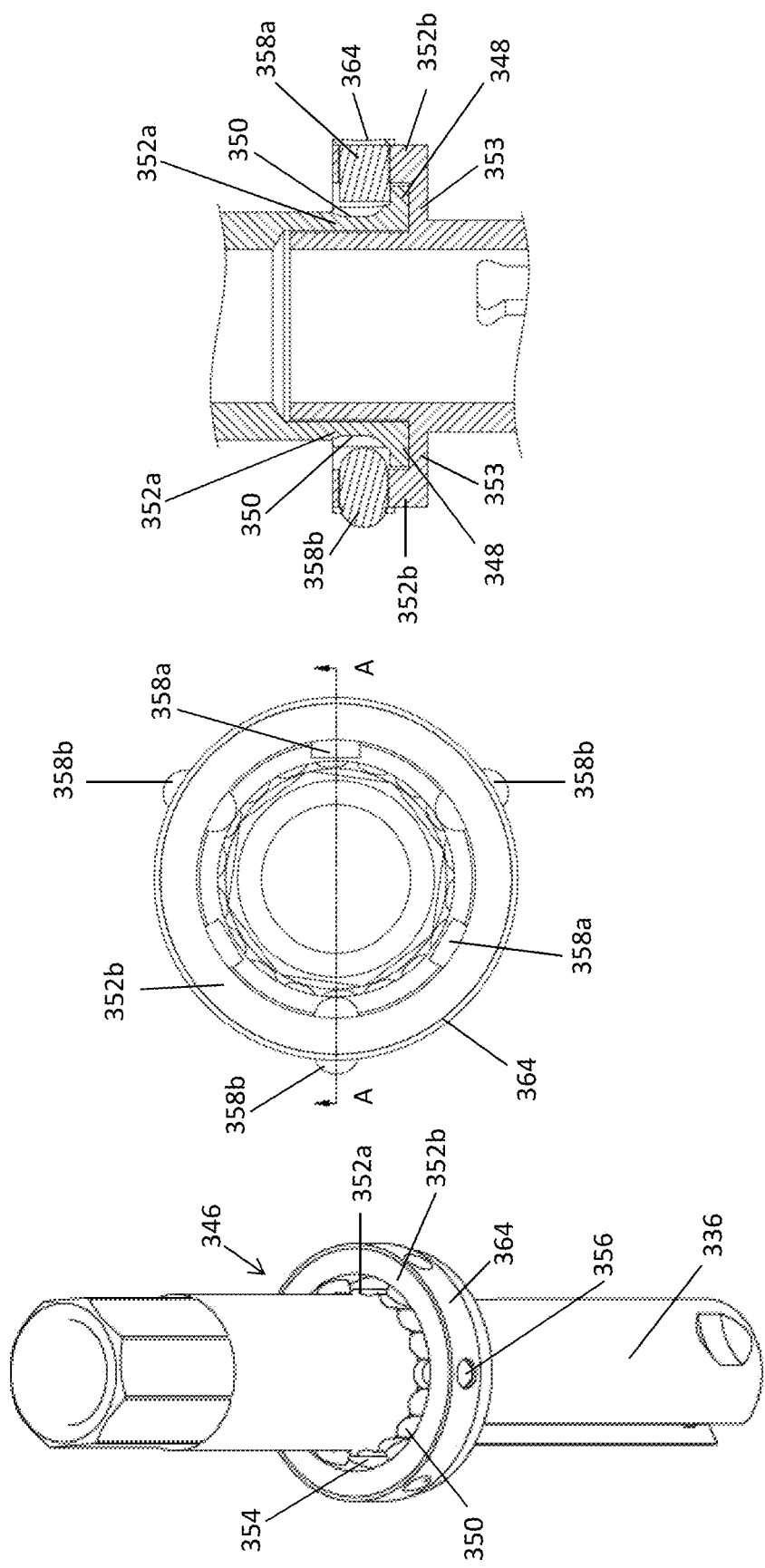

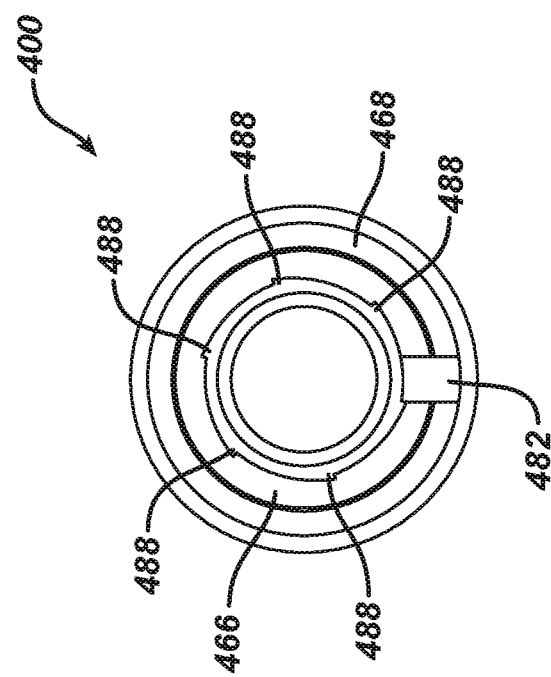
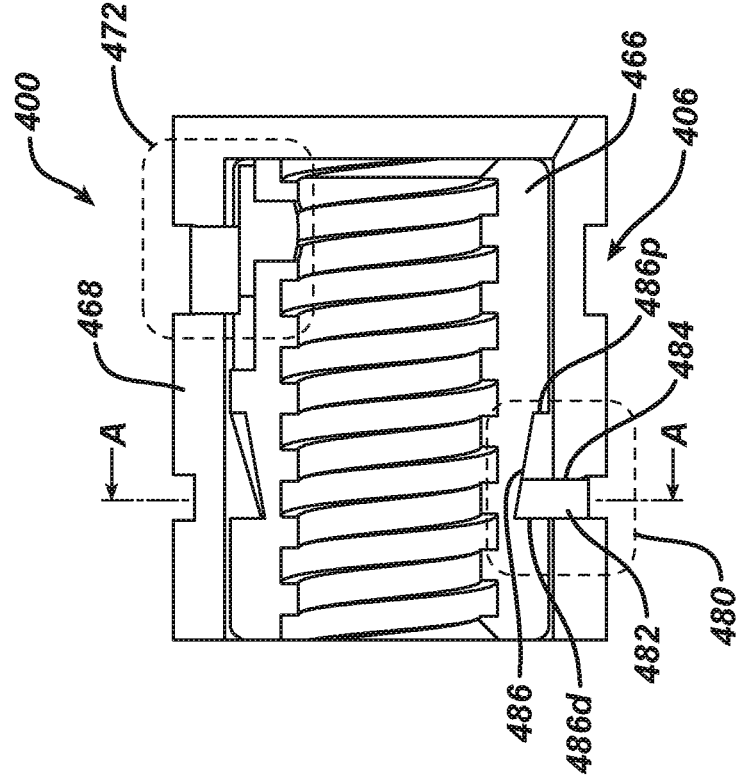

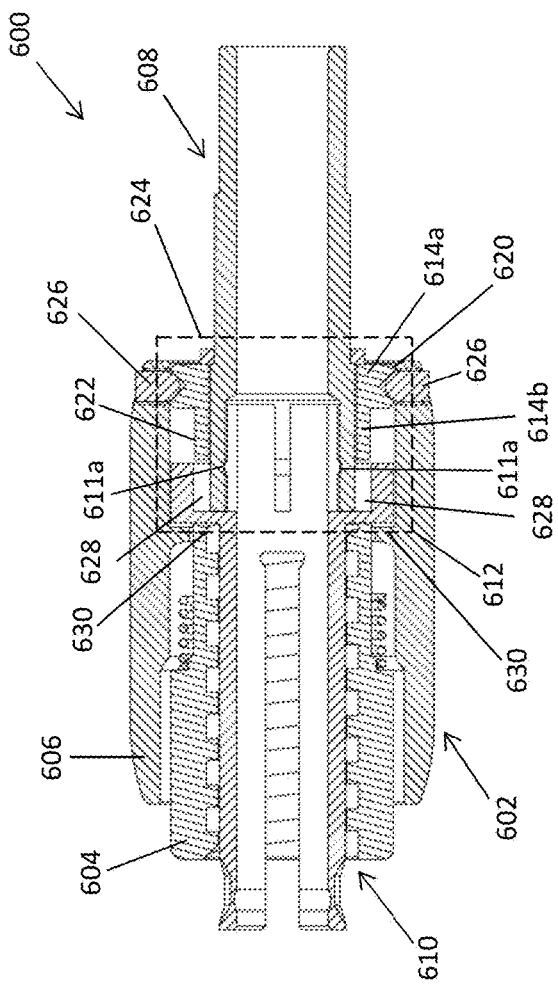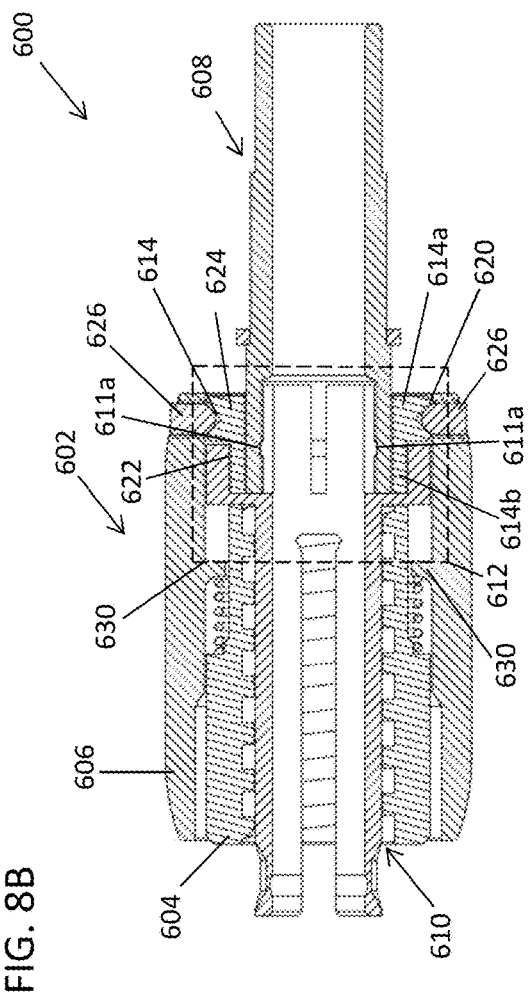

BONE ANCHOR INSERTION INSTRUMENTS AND METHODS

FIELD

Bone anchor insertion instruments and methods are disclosed herein.

BACKGROUND

Bone anchors can be used in orthopedic surgery to fix bone during healing, fusion, or other processes. In spinal surgery, for example, bone anchors can be used to secure a spinal fixation element to one or more vertebrae to rigidly or dynamically stabilize the spine.

In a conventional procedure for coupling a bone anchor to bone, access to the bone is obtained, for example by forming a skin incision and resecting soft tissue disposed over the bone or by using a minimally-invasive technique. A bone anchor assembly is coupled to a bone inserter instrument having a stylet protruding therefrom. The stylet can be docked into bone by tapping or urging the instrument distally towards bone. Once the stylet is advanced to the desired depth, the bone anchor assembly is driven along the path created by the stylet. When the bone anchor assembly is driven to the desired depth, the instrument can be detached from the bone anchor assembly and removed from the incision.

During use, as the bone anchor assembly is being driven into bone, the stylet can continue to advance ahead of the screw. Any further advancement of the stylet can lead to further accidental advancement of the bone anchor assembly into bone. In the event that the bone anchor assembly is driven too deep into the bone, undesired damage to the bone and/or underlying tissue or nerves can result, and consequently, additional unnecessary trauma to the patient.

Accordingly, despite existing technologies, there remains a need for improved instrumentation and methods associated with driving bone anchors into bone.

SUMMARY

Various surgical instruments and methods are disclosed herein for implanting a bone anchor into bone.

In one embodiment, an instrument for driving a bone anchor assembly into bone is provided and can include an anchor drive assembly and a stylet assembly. The anchor drive assembly can include a first handle and an elongate shaft having a distal tip configured to couple to a bone anchor assembly. The stylet assembly can include a second handle and a stylet extending through the elongate shaft. The instrument can have a disengaged position and an engaged position. Rotation of the first handle can be effective to drive the bone anchor assembly into bone only when the instrument is in the engaged position. The rotation of the second handle can be effective to cause axial translation of the stylet relative to the elongate shaft. In one aspect, the instrument can be biased to the disengaged position.

The first handle can also have a variety of configurations. For example, in one aspect, the first handle can be configured to be decoupled from the elongate shaft when the instrument is in the disengaged position such that the first handle is freely rotatable relative to the elongate shaft, and the first handle can be configured to be coupled to the elongate shaft when the instrument is in the engaged position such that rotation of the first handle rotates the elongate shaft.

The stylet can have a variety of configurations. For example, in one aspect, the stylet can be configured to move proximally in response to the bone anchor assembly being driven into bone when the first handle is rotated and the instrument is in the engaged position. In another aspect, the stylet can be configured to axially translate relative to the elongate shaft in response to rotation of the second handle while the first handle is held stationary and the instrument is in the engaged position. In an exemplary embodiment, the stylet assembly can include a carrier coupled to the stylet and disposed within the anchor drive assembly and threadably coupled to the second handle.

In some aspects, the second handle can include an outer sleeve and inner sleeve, and the instrument can be moved from the disengaged position into the engaged position in response to axial movement of the outer sleeve relative to the inner sleeve. In such aspects, for example, the instrument can include a clutch mechanism having a first position and a second position. When the clutch mechanism is in the second position, the clutch mechanism can be configured to couple the first handle to the elongate shaft such that rotation of the first handle rotates the elongate shaft.

In some aspects, a first locking mechanism can lock the outer sleeve to the inner sleeve in a first position, and movement of the stylet to a proximal-most position relative to the elongate shaft can disengage the first locking mechanism to decouple the outer sleeve from the inner sleeve such that the inner sleeve can rotate independently of the outer sleeve. In such aspects, a second locking mechanism can lock the outer sleeve to the inner sleeve in a second position when the first locking mechanism is disengaged, and distal movement of the stylet from the proximal-most position can disengage the second locking mechanism and reengage the first locking mechanism such that the outer sleeve is recoupled to the inner sleeve. In other aspects, the stylet assembly can include a ratchet mechanism that can be configured to lock the outer sleeve to the inner sleeve such that the outer and inner sleeves can rotate simultaneously in one direction to distally move the stylet relative to the elongate shaft.

In another embodiment, a bone anchor inserter instrument is provided and can include an elongate shaft having a distal tip configured to couple to a bone anchor assembly, a stylet extending through the elongate shaft, and a handle assembly coupled to a proximal end of the elongate shaft. The handle assembly can include a first handle, a second handle, and a carrier movably disposed within the handle assembly and coupled to the stylet. The handle assembly can have a first configuration in which the first handle can rotate freely relative to the elongate shaft, and a second configuration in which rotation of the first handle relative to the second handle can cause corresponding rotation of the elongate shaft, and rotation of the second handle relative to the first handle can cause axial translation of the carrier and the stylet coupled thereto.

In some aspects, the stylet can be configured to move proximally in response to rotation of the first handle when the handle assembly is in the second configuration. In other aspects, rotation of the first handle can be effective to drive the bone anchor assembly into bone only when the handle assembly is in the second configuration.

The second handle can have a variety of configurations. For example, in some aspects, the second handle can include outer and inner sleeves. The inner sleeve can be configured to rotate freely relative to the outer sleeve when the handle assembly is in the second configuration and the carrier is in a most-proximal position. In other aspects, the second handle can include an outer sleeve and an inner sleeve and the outer sleeve can be configured to axially move relative to the inner sleeve to move the handle assembly from the first configuration to the second configuration. In such aspects, the instrument can include a clutch mechanism having a first position and a second position. In one aspect, when the clutch mechanism is in the second position, the clutch mechanism can be configured to couple the first handle to the elongate shaft such that rotation of the first handle rotates the elongate shaft.

In some aspects, when the handle assembly is in the second configuration, the carrier can be non-rotatably translatable through the handle assembly in response to rotation of the second handle while the first handle is held stationary. In such aspects, when the handle assembly is in the second configuration, the carrier can be rotatably translatable through the handle assembly in response to rotation of the first handle while the second handle is held stationary.

Methods for implanting a bone anchor assembly are also provided. In one embodiment, the method can include moving a handle assembly on an inserter tool from a first configuration to a second configuration to axially translate a stylet extending through an elongate shaft of the inserter tool, and rotating a first handle of the handle assembly, while maintaining the handle assembly in the second configuration, to thereby adjust a position of a distal tip of the stylet relative to a bone anchor coupled to a distal end of the elongate shaft. The method can also include manipulating the inserter tool to position the distal tip of the stylet in bone, and rotating a second handle of the handle assembly to rotate the elongate shaft and thereby distally advance the bone anchor coupled to the distal end of the elongate shaft along the stylet and into bone. In one aspect, the first handle can be rotated while the handle assembly is maintained in the second configuration. In another aspect, the first handle can include an inner sleeve and an outer sleeve, and moving the handle assembly from the first configuration to the second configuration can include moving the outer sleeve relative to the inner sleeve in an axial direction. In another aspect, rotating the second handle can be effective to cause axial translation of the stylet in a proximal direction relative to the elongate shaft.

In some aspects, moving the handle assembly from the first configuration to the second configuration can cause a clutch mechanism to move from a disengaged position to an engaged position. In another aspect, moving the handle assembly from the first configuration to the second configuration can cause the second handle to mate to the elongate shaft such that rotation of the second handle rotates the elongate shaft.

BRIEF DESCRIPTION OF THE DRAWINGS

The invention will be more fully understood from the following detailed description taken in conjunction with the accompanying drawings, in which:

FIG. 1A is a top view of one embodiment of a surgical instrument that includes an anchor assembly having a driving tube assembly, and a stylet assembly with a clutch assembly, showing the surgical instrument in a disengaged position;

FIG. 1B is an embodiment of a first handle that can be coupled to a proximal driving tube of the drive tube assembly of FIG. 1A;

FIG. 1C is another embodiment of a first handle that can be coupled to the proximal driving tube of the drive tube assembly of FIG. 1A;

FIG. 1E is a cross-sectional view of the surgical instrument of FIG. 1A taken at A-A;

FIG. 1F is a magnified view of a portion of the surgical instrument in FIG. 1E taken at 1F;

FIG. 2C is a magnified view of a portion of the surgical instrument in FIG. 2B taken at 2C;

FIG. 4A is a perspective view of another embodiment of a driving tube assembly and a clutch assembly;

FIG. 4B is a cross-sectional view of the driving tube assembly and the clutch assembly of FIG. 4A;

FIG. 4C is a cross-sectional view of FIG. 4B taken at A-A, showing a flange that is coupled to a portion of the driving tube assembly;

FIG. 5A is a perspective view of another embodiment of a driving tube assembly and a clutch assembly;

FIG. 5B is a cross-sectional view of the driving tube assembly and the clutch assembly of FIG. 5A;

FIG. 5C is a cross-sectional view of FIG. 5B taken at A-A, showing a flange that is coupled to a portion of the driving tube assembly;

FIG. 6A is a partial, cross sectional view of another embodiment of a surgical instrument that includes a ratchet mechanism;

FIG. 6B is a cross sectional view of the surgical instrument of FIG. 6A taken at A-A;

FIG. 8A is a partial, cross-sectional side view of another embodiment of a surgical instrument having a clutch assembly having a hexagonal design, showing the surgical instrument in the disengaged position;

FIG. 8B is a cross-sectional view of the surgical instrument of FIG. 8A, showing the surgical instrument in an engaged position.

DETAILED DESCRIPTION

Figure 1D:
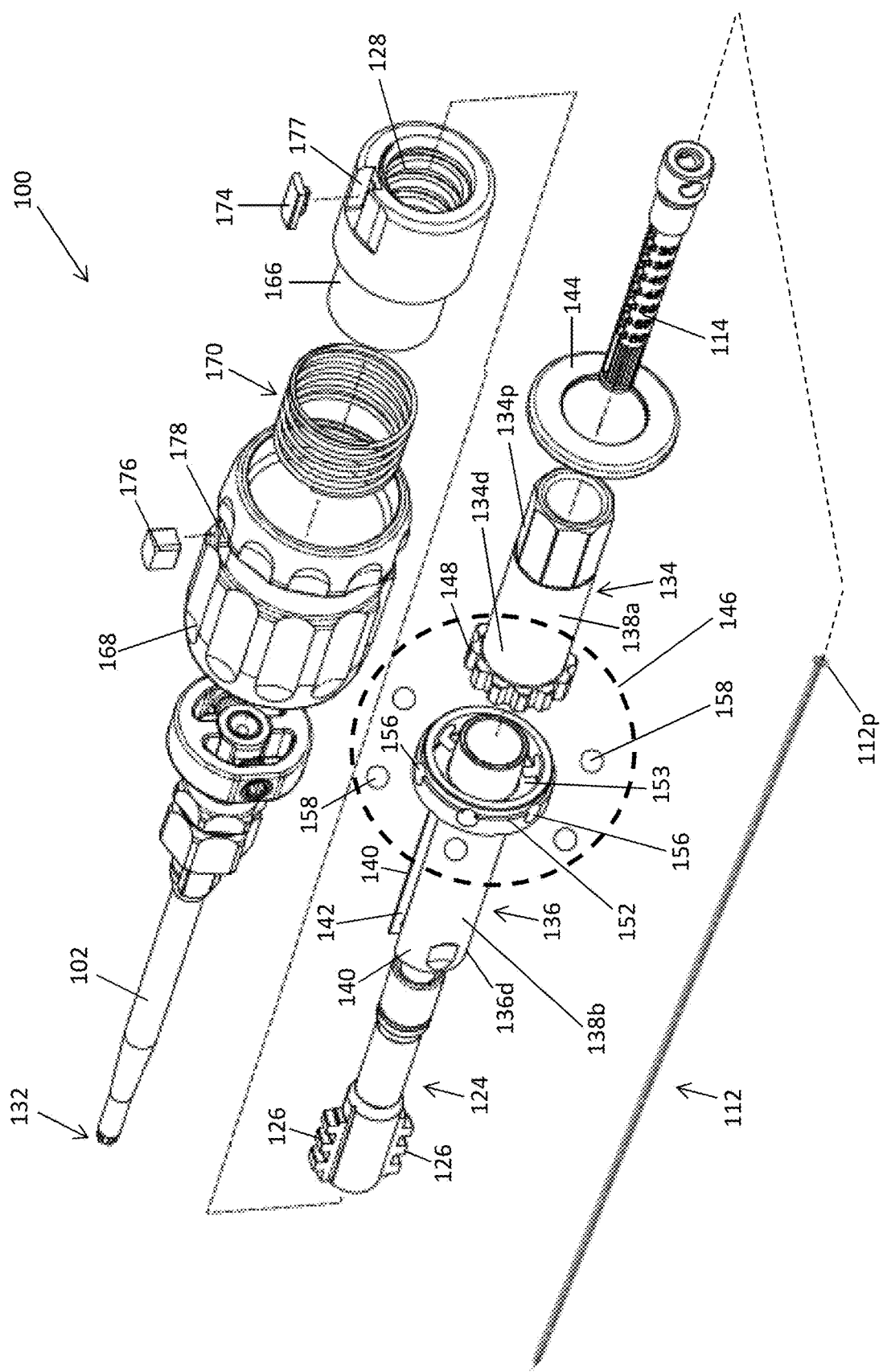
FIG. 1D is an exploded view of the surgical instrument of FIG. 1A.
Figure 1H:
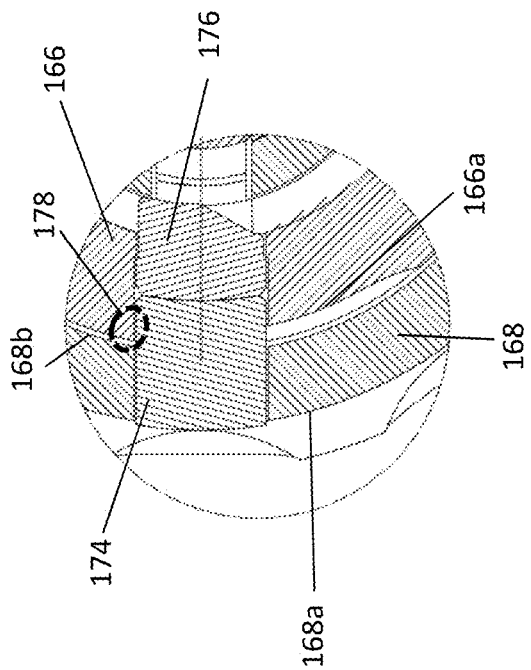
FIG. 1H is a magnified view of a portion of the surgical instrument in FIG. 1G taken at 1H.
Figure 1G:
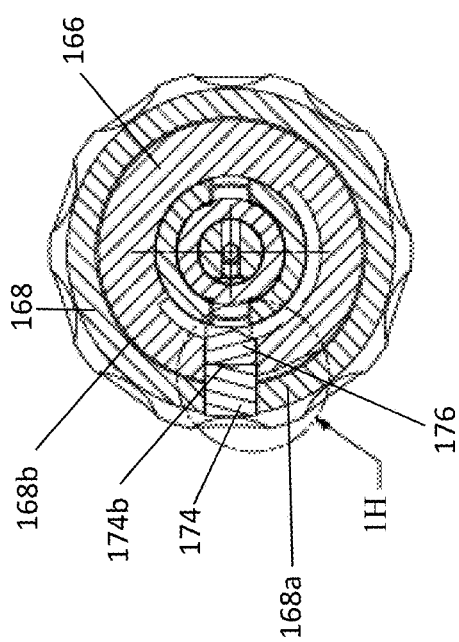
FIG. 1G is another cross-sectional view of the surgical instrument of FIG. 1A taken at B-B.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Surgical instruments and methods are provided for driving a bone anchor assembly into bone. In general, a bone screw inserter instrument is provided having a disengaged position and an engaged position. As discussed in greater detail below, the instrument can be configured such that the instrument can only drive a bone anchor assembly into bone when the instrument is in the engaged position. In certain exemplary aspects, the instrument can include an anchor drive assembly having a first handle and an elongate shaft with a distal tip that is configured to couple to a bone anchor assembly. When the instrument is in the disengaged position, the first handle can be decoupled from the elongate shaft such that the first handle can freely rotate relative to the elongate shaft. When the instrument is in the engaged position, however, the first handle can be coupled to the elongate shaft such that rotation of the first handle can be effective to drive the bone anchor assembly into bone. As such, unless the instrument is in the engaged position, rotation of the first handle will not effect rotation of the elongate shaft, and consequently, drive the bone anchor assembly into bone. The instrument can also include a stylet assembly that includes a second handle and a stylet that extends through the elongate shaft. Rotation of the second handle can be effective to cause axial translation of the stylet relative to the elongate shaft when either the instrument is in the engaged position or when the elongate shaft is held stationary. Further, the second handle can be movable from a first position to a second position to cause the instrument to move from the disengaged position to the engaged position. As a result, the instrument can only be moved into and maintained in its engaged position when the second handle is held in the second position. Thus, the bone anchor inserter instrument can allow the bone anchor assembly to be driven into bone while also preventing the stylet from advancing ahead of the bone anchor assembly. That is, unlike conventional bone inserter instruments, the bone anchor inserter instrument can be configured to control the advancement of the stylet such that the stylet is unable to further advance into bone as the bone anchor assembly is being implanted.

An exemplary bone anchor inserter instrument can include a variety of features to facilitate implantation of a bone anchor assembly, as described herein and illustrated in the drawings. However, a person skilled in the art will appreciate that the bone anchor inserter instruments can include only some of these features and/or it can include a variety of other features known in the art. The bone anchor inserter instruments described herein are merely intended to represent certain exemplary embodiments.

FIGS. 1A-2E illustrate an exemplary embodiment of a surgical instrument 100 that is configured to prevent advancement of a stylet when driving a bone anchor assembly into bone. As described in more detail below, the bone anchor assembly cannot advance into bone without retraction of the stylet. The illustrated surgical instrument 100 generally includes an anchor drive assembly for driving a bone anchor into bone, and a stylet assembly extending therethrough for controlling positioning of a style relative to the bone anchor.

In general, the anchor drive assembly includes an elongate shaft 102 having a distal tip 132 configured to couple to a bone anchor assembly (not shown). The anchor drive assembly can also include a proximal driving tube 134 and a distal driving tube 136. A proximal end 102p of the elongate shaft 102 can be coupled to a distal end 136d of the distal driving tube 136, and the proximal driving tube 134 can be coupled to a proximal end 136p of the distal driving tube 136 via a clutch assembly 146, which will be discussed in more detail below. A first handle, also referred to as a proximal handle 110, e.g., 110a or 110b as shown in FIGS. 1B and 1C, can be mated to a proximal end 134p of the proximal driving tube 134, as shown in FIGS. 1E-1F and 2B-2C. The clutch assembly 146 can have a disengaged position in which the first handle 110 is decoupled from and rotates independent of the elongate shaft 102, and an engaged position in which the first handle 110 is coupled to and rotates with the elongate shaft 102. In the engaged positioned, rotation of the first handle 110 can thus cause corresponding rotation of the proximal driving tube 134.

The stylet assembly can generally include a stylet 112 having a proximal end 112p that removably couples to a depth adjuster 114. The depth adjuster 114 can mate to a carrier 124, which can be disposed within the distal drive tube 136. The carrier 124 can extend through the distal drive tube 136 to threadably engage with a portion of a second handle, also referred to as a distal handle, 106, and in particular with an inner sleeve 166 of the second handle 106.

Figure 2A:
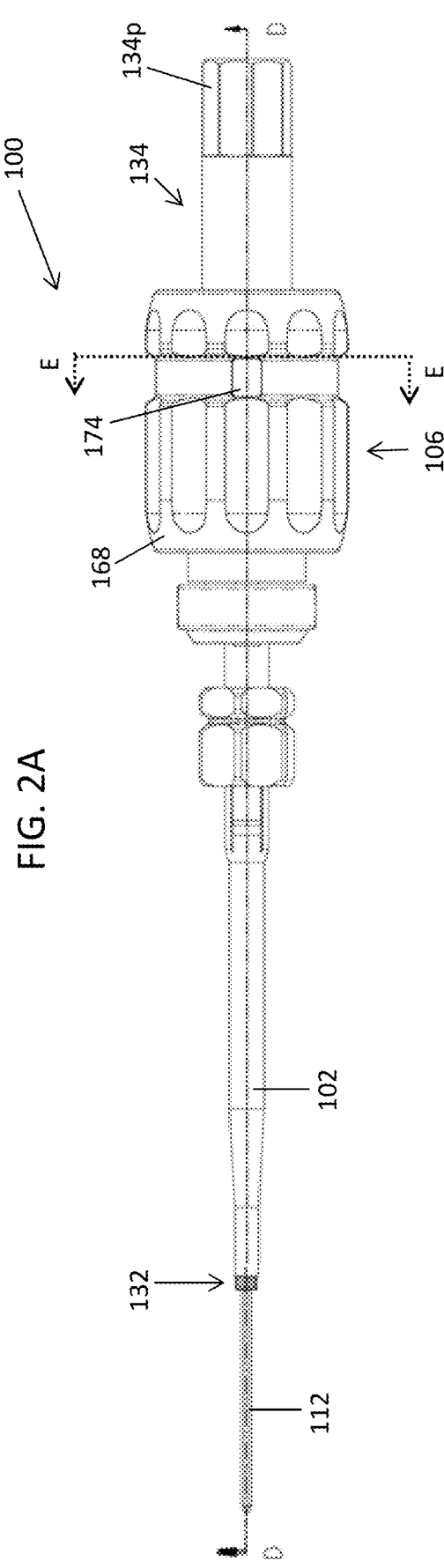
FIG. 2A is a top view of the surgical instrument of FIG. 1A in an engaged position and having a carrier at its proximal-most position.
Figure 2B:
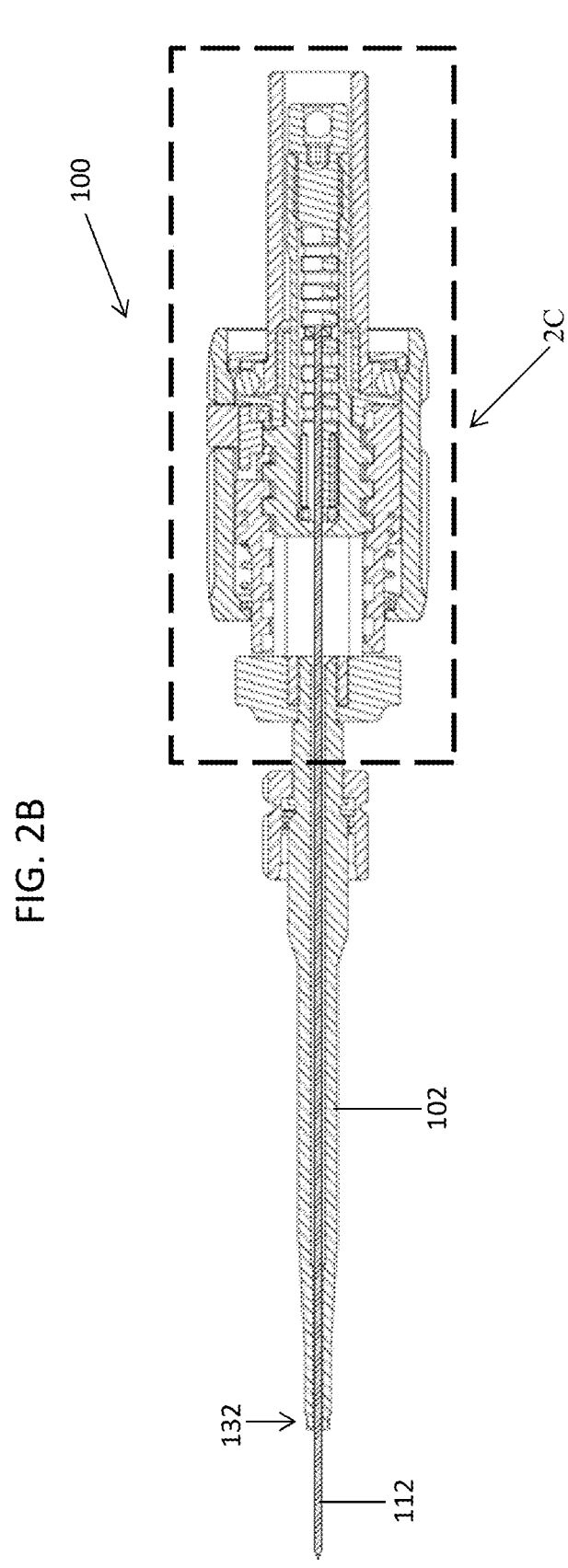
FIG. 2B is a cross-sectional view of the surgical instrument of FIG. 2A taken at D-D.

The second handle 106 can also include an outer sleeve 168 disposed around the inner sleeve 166. A locking mechanism, discussed in more detail below, can couple between the inner and outer sleeves 166, 168. When the locking mechanism is in the locked position, rotation of the outer sleeve 168 can cause corresponding rotation of the inner sleeve 166, which in turn will cause axial translation of the carrier 124 through the distal drive tube 136. Such movement of the carrier 124 will thereby adjust the position of the stylet 112. When the carrier 124 is moved to its proximal-most position, as shown in FIGS. 2B and 2C, it can be configured to cause the locking mechanism to move to an unlocked configuration, thereby decoupling the outer sleeve 168 from the inner sleeve 166, thus allowing continued rotation of the outer sleeve 168 without causing further movement of the carrier 124 and stylet 112. The outer sleeve 168 can also be configured to control the clutch mechanism. As will be explained in detail below, the outer sleeve 168 can be biased distally, and it can be configured to move proximally to move the clutch mechanism from the disengaged position to the engaged position. Thus, when the outer sleeve 168 is moved and held in a proximal position to maintain the clutch mechanism in the engaged position, rotation of the first handle 110 relative to the second handle 106 will cause the elongate shaft 102 to rotate for driving a bone anchor into bone while also causing retraction of the stylet 112.

As indicated above, the stylet assembly can have a variety of configurations. With reference to FIGS. 1D-1F and 2B-2C, the proximal and distal driving tubes 134, 136 can each be in the form of an elongated tubular member having an inner lumen extending therethrough. As shown in FIG. 1D, the distal driving tube 136 can have two legs 140 that are separated by opposed through slots 142 that extend through a wall of the distal driving tube 136. In certain embodiments, a washer 144 can be provided for coupling the proximal and distal driving tubes 134, 136. In particular, the washer 144 can be configured to be affixed or threaded to the distal driving tube 136 and it can engage a flange 148 of the proximal driving tube 134 to prevent the tubes 134, 136 from axially translating relative to each other. While the washer 144 prevents translational movement of the proximal and distal driving tubes 134, 136, the tubes 134, 136 can rotate relative to each other. The clutch mechanism, discussed in more detail below, can be configured to rotatably couple and decouple the proximal and distal drive tubes 134, 136.

The carrier 124 of the stylet assembly can be disposed within the distal driving tube 136, and it can facilitate positioning of the stylet 112 relative to a bone anchor assembly coupled to the elongate shaft 102. The carrier 124 can have a variety of configurations. In the illustrated embodiment, the carrier 124 has a generally cylindrical configuration and is cannulated with an inner lumen extending therethrough. As shown in FIGS. 1E-1F and 2B-2C, the carrier 124 can be slidably disposed within the distal driving tube 136. The carrier 124 can thus have an outer diameter that is less than an inner diameter of the inner lumen of the distal driving tube 136 to allow the carrier 124 to be disposed therein. The carrier 124 can include one or more thread features 126 formed on an outer surface of the carrier 124. As shown in FIG. 1D, the one or more thread features 126 are formed on opposed sides of the carrier 124 and do not extend fully circumferentially around the carrier 124. The opposed thread features 126 can extend through opposed slots 142 formed in the distal driving tube 136. The opposed thread features 126 can engage corresponding internal threads 128 of the inner sleeve 166 of the second handle 106, as will be discussed in more detail below. Such a configuration will allow the opposed thread features 126, and thus the carrier 124, to translate axially along the distal driving tube 136 in response to rotation of the second handle 106, yet it will prevent rotation of the carrier 124 relative to the distal driving tube 136, and thus the elongate shaft 102.

For example, when the surgical instrument 100 is in the engaged position and the first handle 110 is held stationary, rotation of the second handle 106 can cause the internal threads 128 to interact with the opposed thread features 126 on the carrier 124. This interaction can cause the carrier 124 to non-rotatably translate axially along the distal driving tube 136 and relative to the elongate shaft 102. That is, when the surgical instrument 100 is in the engaged position, the carrier 124 is non-rotatably translatable through the distal driving tube 136 in response to rotation of the second handle 106 while the first handle 110 is held stationary. Alternatively, the elongate shaft 102 can be held stationary while the second handle 106 is being rotated independent of the surgical instrument 100 being in the disengaged or engaged position.

Further, when the surgical instrument 100 is in the engaged position and the second handle 106 is held stationary, the rotation of the first handle 110 can cause corresponding rotation of the distal driving tube 136 which will force the carrier 124 to rotate and thus move in a proximal direction, thereby retracting the stylet 112. The interaction between the internal threads 128 of the second handle 106 and the opposed thread features 126 on the carrier 124 will thus cause the carrier 124 to rotatably translate axially along the distal driving tube 136 and thus relative to the elongate shaft 102. That is, when the surgical instrument 100 is in the engaged position, the carrier 124 is rotatably translatable through the distal driving tube 136 in response to rotation of the first handle 110 while the second handle 106 is held stationary.

The depth adjuster 114 can be mated to the carrier 124 for moving with the carrier 124, and the stylet 112 can be mated to the depth adjuster 114. Various configurations for the stylet 112 and depth adjuster 114, as well as techniques for mating the depth adjuster 114 to the carrier 124, are disclosed in more detail in U.S. patent application Ser. No. 15/633,958 entitled "Spinal Screw Insertion Device and Methods," which is incorporated by reference herein in its entirety. In certain exemplary embodiments, the stylet 112 can have an elongate configuration with a pointed distal tip to facilitate insertion into bone. A person skilled in the art will appreciate that in other embodiments the stylet 112 can mate directly to the carrier 124.

The positioning of the stylet 112 relative to the elongate shaft 102, such as to allow a length of stylet 112 to extend from the distal end 102d of the elongate shaft 102, can be effected by the rotation of the second handle 106. The second handle 106 can have an inner sleeve 166, an outer sleeve 168, and a biasing element 170. In this exemplary embodiment, the inner sleeve 166 includes internal threads 128 and the outer sleeve 168 is disposed about and is designed to axially translate relative to the inner sleeve 166. As shown, the biasing element 170 is in the form of helical spring that is housed within the second handle 106 between the outer sleeve 168 and the inner sleeve 166. The biasing element 170 can bias the outer sleeve 168 distally, thereby biasing the second handle 106 to a first position (home position).

As the bone anchor assembly is being driven into bone, the stylet 112 retracts until it reaches its proximal-most position relative to the elongate shaft 102. That way, the stylet 112 can be prevented from advancing with or ahead of the bone anchor assembly as the bone anchor assembly is being implanted. As such, in one embodiment, retraction of the stylet 112 can be effected by the rotation of the first handle 110. For example, when the instrument 100 is in the engaged position and the second handle 106 is being held stationary, the stylet 112 can proximally retract relative to the elongate shaft 102 in response to rotation of the first handle 110.

Figure 2E:
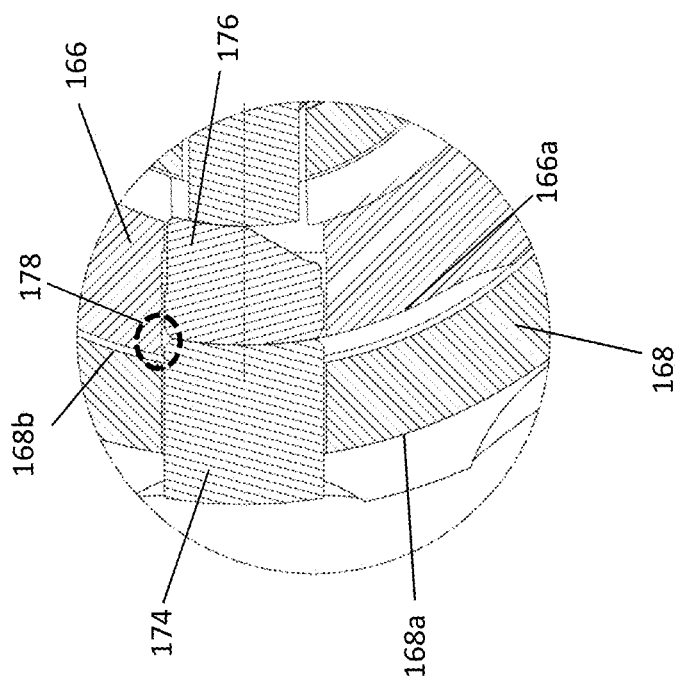
FIG. 2E is a magnified view of a portion of the surgical instrument in FIG. 2D taken at 2E.
Figure 2D:
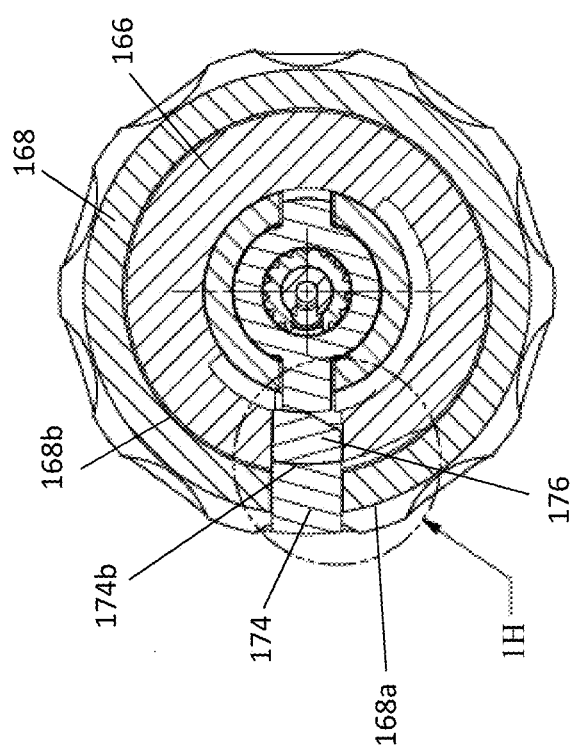
FIG. 2D is another cross-sectional view of the surgical instrument of FIG. 2A taken at E-E.

Further, independent of the instrument being in the disengaged or engaged position, the outer sleeve 168 can be locked to the inner sleeve 166 by way of a locking assembly 172. While the locking assembly 172 can have a variety of configurations, in this exemplary embodiment, the locking assembly 172 includes a first locking mechanism that includes a spring pin 174 and a tumbler pin 176 that are positioned within a channel 177 that extends through the second handle 106 (e.g., extends through the outer and inner sleeves 166, 168) to lock the inner sleeve 166 and the outer sleeve 168 in a first position. As shown in FIGS. 1E-1H, a first surface 174a of the spring pin 174 is flush with a first surface 168a of the outer sleeve 168, and a second surface 174b of the spring pin 174 abuts the tumbler pin 176. When the second handle 106 is rotated to cause the carrier 124 to translate proximally within the distal drive tube 136, the carrier 124 will eventually reach a proximal-most position relative to the distal drive tube 136. As the carrier 124 reaches its proximal-most position, at least one of the one or more thread features 126 of the carrier 124 comes in contact with the tumbler pin 176 and pushes the tumbler pin 176, and thus the spring pin 174, radially outward relative to the second handle 106. This causes the tumbler pin 176 to align with an outer surface 166a of the inner sleeve 166, as shown in FIGS. 2D-2E, and consequently disengages the first locking mechanism. This disengagement causes decoupling of the outer sleeve 168 from the inner sleeve 166. In the proximal-most position, the stylet 112 is fully retracted relative to the bone anchor assembly, and thus there is no risk of advancing the stylet 112 into bone beyond the bone anchor assembly. When the outer sleeve 168 is decoupled from the inner sleeve 166, the inner sleeve 166 can rotate independently of the outer sleeve 168. In this way, the user can hold the outer sleeve 168 with the carrier 124 at its proximal-most position while also rotating the first handle 110 to continue to drive a bone anchor assembly into bone, as will be discussed in more detail below. Otherwise, once the stylet 112 reaches its proximal-most position, the surgical instrument 100 would jam and the user would not be able to continue to rotate the first handle 110 to distally drive the bone anchor assembly into bone.

In some embodiments, the locking assembly 172 can include a second locking mechanism to lock the inner sleeve 166 and the outer sleeve 168 in a second position independent of the instrument being in the disengaged or engaged position. For example, as shown in FIGS. 1G-1H and 2D-2E, the inner sleeve 166 can have an engagement element 178 that is formed on its outer surface 166a when the spring and tumbler pins 174, 176 are pushed radially outward relative to the elongated shaft 102. This engagement element 178 allows the inner sleeve 166 to rotate relative to the outer sleeve 168 only in a first direction. This first direction corresponds to the first direction in which the first handle 110 rotates to drive the bone anchor assembly into bone. When the first handle 110 is rotated in the opposite direction, e.g., a second direction, the spring pin 174 engages the engagement element 178 and prevents the inner sleeve 166 from rotating in the second direction without causing the outer sleeve 168 to rotate in the same direction in tandem. That is, once the spring pin 174 engages the engagement element 178, the inner and outer sleeves 166, 168 will recouple to move simultaneously in the second direction. As the inner and outer sleeves 166, 168 begin to the move in the second direction in tandem, the stylet 112 will begin to distally advance relative to the elongate shaft 102, thereby disengaging the second locking mechanism while reengaging the first locking mechanism, and consequently, relocking the outer sleeve 168 and inner sleeve 166 in the first position.

While the second handle is used to control the stylet assembly, as indicated above the first handle can control the bone anchor drive assembly. With reference to FIGS. 1A, 1D-1F and 2A-2B, the elongate shaft 102 of the anchor drive assembly has a generally elongate configuration with a distal tip 132 configured to engage a bone anchor, and a proximal end 102p that can couple to the distal end 136d of the distal drive tube 136, which in turn can be coupled to the proximal drive tube 238 by a clutch assembly. The distal drive tube 136 can be in the form of a generally elongate hollow tube having opposed slots 142 extending along a length thereof for receiving the opposed thread features 126 on the carrier 124 therethrough. The proximal drive tube 134 can also be in the form of a generally elongate tube. A proximal end 134p of the proximal drive tube 134 can include an engagement feature formed thereon, such as a hex feature, for mating with a corresponding feature formed within the first handle 110.

Figure 3C:
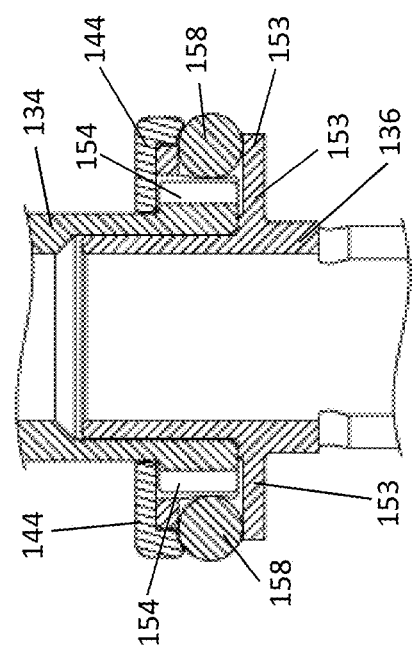
FIG. 3C is a cross-sectional view of FIG. 3B taken at A-A, showing a flange that is coupled to a portion of the driving tube assembly.
Figure 3B:
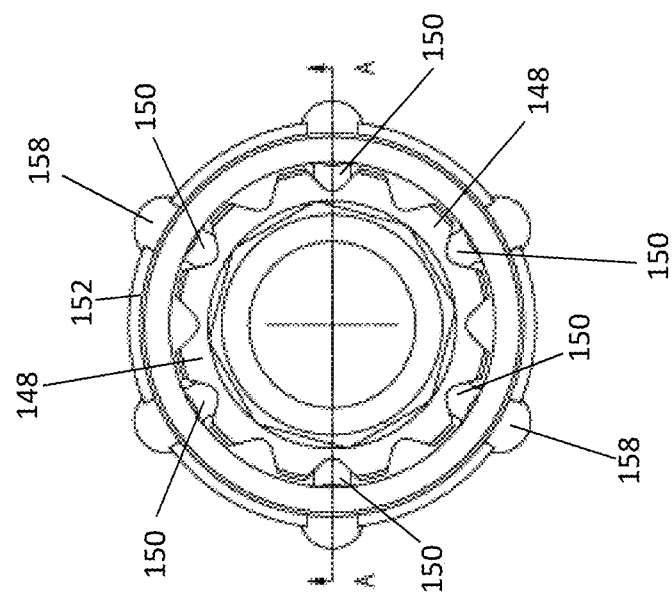
FIG. 3B is a cross-sectional view of the driving tube assembly and the clutch assembly of FIG. 3A.
Figure 3A:
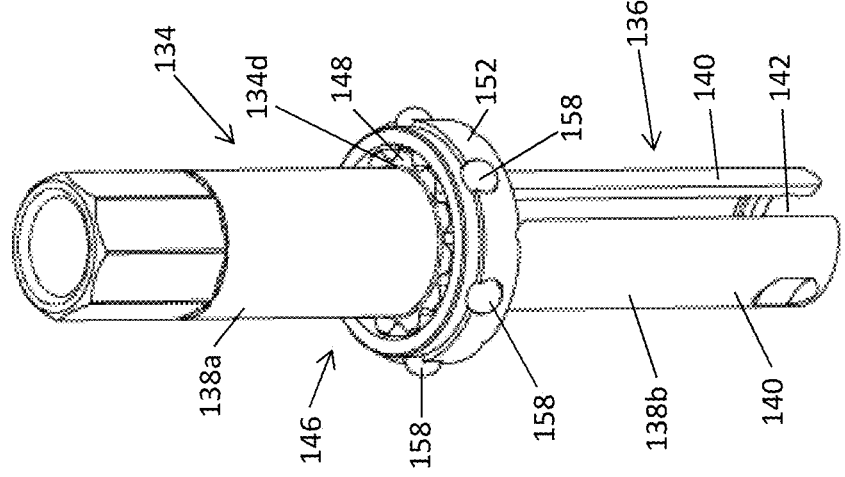
FIG. 3A is a perspective view of the driving tube assembly and the clutch assembly of the surgical instrument shown in FIGS. 1A-1H.

As indicated above, and as shown in FIGS. 1B-1F and 2B-2C, and in further detail in FIGS. 3A-3C, the clutch mechanism can be coupled between the proximal and distal driving tubes 134, 136 in a manner that allows the tubes 134, 136 to selectively rotate together. When the clutch mechanism is in a disengaged position (e.g., a first position), the first handle 110 rotates freely relative to the elongate shaft 102, and vice versa, resulting in the inability to distally advance the bone anchor assembly into bone by rotation of the first handle 110. When the clutch mechanism is in an engaged position (e.g., a second position) and the driving tubes 134, 136 are coupled, the first handle 110 will couple to the elongate shaft 102 such that the rotation of the first handle 110 can cause the elongate shaft 102 to rotate for driving a bone anchor assembly into bone, and consequently, proximal retraction of the stylet 112.

As shown, the clutch mechanism can include a clutch assembly 146 having a flange 148 with one or more recessed channels 150. The flange 148 extends radially outward from the distal end 134d of the proximal driving tube 134. The clutch assembly 146 can further include an annular ring 152 that is positioned about a proximal portion of the distal driving tube 136. In the illustrated embodiment, the annular ring 152 has a base portion 153 that extends radially outward from the distal driving tube 136 to thereby create an annular channel 154 that extends fully circumferentially around the distal driving tube 136. As shown, the flange 148 rests within this annular channel 154, and is maintained within this annular channel 154 via the washer 144. That is, the washer 144, which is affixed about the top portion of the annular ring 152, maintains the flange 148 within the annular channel 154 to prevent axial translation of the proximal and distal driving tubes 134, 136 relative to each other. The washer 144, however, by being non-affixed to the flange 148, allows for rotational movement of the proximal and distal driving tubes 134, 136 relative to each other.

Further, the annular ring 152 can also include one or more through holes 156 to receive a corresponding engagement feature 158. Each of the one or more through holes 156 can allow a corresponding engagement feature 158 to extend therethrough and engage the recessed channels 150 of the flange 148 when the second handle 106 is moved from a first position to a second position (e.g., its proximal-most position). The washer 144 can also function as a retention feature that is configured to prevent the engagement features 158 from moving radially outward once the engagement features are positioned partially within the annular ring 152. The one or more through holes 156 and corresponding engagement features 158 can be of various shapes and sizes so long as the corresponding engagement features 158 can extend through the through hole 156. In this exemplary embodiment, the engagement features 158 are spherically shaped.

In use, the surgical instrument 100 can be moved from a disengaged position (FIGS. 1A-1H) to an engaged position (FIGS. 2A-2E). When in the disengaged position (FIGS. 1A-1H), the first handle 110 and the elongate shaft 102 are decoupled, and therefore the first handle 110 can freely rotate relative to the elongate shaft 102. When in the engaged position (FIGS. 2A-2E), however, the first handle 110 is coupled to the elongate shaft 102 such that rotation of the first handle 110 rotates the elongate shaft 102, and in turn, drives a bone anchor assembly that is coupled to the elongate shaft 102 into bone while also retracting the stylet 112 to its proximal-most position. It should be noted that although the surgical instrument 100 is illustrated in FIGS. 2A-2E with the carrier 124 in its proximal-most position and the first locking mechanism disengaged, this is not required for the surgical instrument 100 to be in the engaged position. That is, the surgical instrument can be in the engaged position independent of the position of the carrier and the disengagement/engagement of the first locking mechanism.

The surgical instrument 100 can be moved from the disengaged position (FIGS. 1A-1H) to the engaged position (FIGS. 2A-2E) by moving (e.g. pulling) the second handle 106 in a proximal direction (e.g., towards the first handle 110). In particular, the axial translation of the outer sleeve 168 from its first position (home position) to a second position can cause the biasing element 170 to move from a first position to a second position to thereby allow engagement of the clutch assembly 146, and consequently moving the instrument 100 from its disengaged position to its engaged position. In this way, the pulling force applied by a user can overcome the biasing force of the biasing element 170 to allow the outer sleeve 168 to move in a proximal direction. As such, the clutch assembly 146 becomes engaged when the outer sleeve 168 is moved from its first position to its second position causing the engagement features 158 to slide into engagement with the recessed channels 150 of the flange 148.

For example, as the outer sleeve 168 is being moved in a proximal direction, the engagement features 158 slide along a tapered portion 160 of the inner surface of the outer sleeve 168. As the outer sleeve 168, and thus the second handle 106, reaches its proximal-most position (FIGS. 2A-2E), the engagement features 158 come in contact with a non-tapered portion 162 of the inner surface of the outer sleeve 168 that pushes the engagement features 158 radially inward, causing the engagement features 158 to engage the recessed channels 150 of the flange 148. Once the engagement features 158 are at least partially positioned within the recessed channels 150, the proximal driving tube 134 becomes rotatably engaged with the distal driving tube 136. Consequently, the first handle 110 is therefore coupled to the elongate shaft 102, and as a result, the first handle 110 can rotate the elongate shaft 102 to drive a bone anchor assembly into bone.

Once the surgical instrument 100 is in the engaged position (FIGS. 2A-2E), distal movement of the outer sleeve 168 allows the outer sleeve 168 to return to its first position, and consequently the biasing element 170. This movement of the outer sleeve 168 disengages the clutch assembly 146 and allows the surgical instrument 100 to move from its engaged position back to its disengaged position. In particular, when the outer sleeve 168 is moved back to its first position, the engagement features 158 move radially outward and disengage the recessed channels 150 of the flange 148, thereby disengaging the clutch assembly 146.

For example, in use, when the outer sleeve 168 is in its second position (FIGS. 2A-2E), a user can release the outer sleeve 168 (e.g., stop applying a pulling force to the outer sleeve 168 towards the first handle 110). This causes the biasing element 170 to distally advance, and thus the outer sleeve 168, back towards its first position. In this way, by moving the outer sleeve 168 in a distal direction, e.g., by the user releasing the outer sleeve 168, the biasing element 170 returns to its first position, and consequently, the instrument 100 returns to its disengaged position.

As mentioned above, the surgical instrument 100 includes a clutch mechanism that can be configured to couple the proximal and distal driving tubes 134, 136 when the instrument is in the engaged position. As shown in detail in FIGS. 3A-3C, the clutch mechanism can include a clutch assembly 146 having a bearing configuration. In other embodiments, the clutch assembly can have a gear pin configuration (FIGS. 4A-4C) or a dowel pin configuration (FIGS. 5A-5C). It is also contemplated that the clutch assembly 146 can include configurations other than those described below.

FIGS. 4A-4C illustrates an exemplary embodiment of a clutch assembly 246 having a gear pin configuration. The clutch assembly 246 is similar to clutch assembly 146 except for the flange, the through holes, and the engagement features. In this embodiment, the engagement features 258 are gear pins that are configured to extend through rectangular shaped through holes 256 and mesh with teeth 250 of the flange 248. The engagement and disengagement of the engagement features 258 are similar to engagement and disengagement of engagement features 158 (FIGS. 1D-1F and 2B-2C) and are therefore not described in detail herein. Further, the engagement features 258 each include a flange 259 that is configured to retain the engagement features 258 within the holes 256 and prevent the engagements features 258 from moving radially outward once they are positioned within the holes 256. Thus, in this embodiment, while the washer 244 can be provided for axial securement of the proximal drive tube with the distal driving tube, the flange 259 is provided for the retention of the engagement features 258.

FIGS. 5A-5C illustrate an exemplary embodiment of a clutch assembly 346 having a dowel pin configuration. In this illustrated embodiment, the clutch assembly 346 can include a first annular ring 352a having one or more recessed channels 350 about the distal end 334d of the proximal driving tube 334. The clutch assembly 346 can further include a second annular ring 352b that is positioned about the distal driving tube 336. The second annular ring 352b can have a base portion 353 that extends radially outward from the distal driving tube 336 to thereby create an annular channel 354 that extends fully circumferentially around the distal driving tube 336. As shown, the first annular ring 352a rests within this annular channel 354.

The second annular ring 352b can also include one or more through holes 356 to receive one or more first engagement features 358a and one or more second engagement features 358b. In this exemplary embodiment, the one or more first engagement features 358a is a set screw that can be configured to couple the proximal driving tube 334 to the distal driving tube 336 by engaging the second annular ring 352b of the distal driving tube 336. In particular, each set screw extends through the corresponding through hole 356 and engages with a flange 348 extending radially outward from the distal end 364p of the proximal driving tube 334. This engagement functions as an axial retention mechanism to prevent separation of the proximal and distal driving tubes 334, 336. The one or more first engagement features 358a are set in place by an annular collar 364 that is positioned about the outer surface of the second annular ring 352b. The annular collar 364 can include one or more through holes 356 configured to receive the one or more second engagement features 358b. As shown, the one or more second engagement features 358b are elliptically shaped. The engagement and disengagement of the one or more second engagement features 358b are similar to engagement and disengagement of engagement features 158 (FIGS. 1D-1F and 2B-2C) and is therefore not described in detail herein.

FIGS. 6A-6B illustrate another embodiment of a surgical instrument. Aside from the differences described in detail below, the surgical instrument 400 can be similar to the surgical instrument 100 (FIGS. 1A-2E) and is therefore not described in detail herein. Further, for purposes of simplicity, certain components of the surgical instrument 400 are not illustrated in FIG. 6A-6B.

As shown, the surgical instrument 400 includes a locking assembly 472 having a locking mechanism, and a ratchet mechanism having a ratchet assembly 480. The locking mechanism can be similar to the first locking mechanism as shown in FIGS. 1D-1F and 2A-2C, and is therefore not described in detail herein.

While the ratchet mechanism can have a variety of configurations, in this embodiment, the ratchet mechanism includes a ratchet assembly 480. The ratchet assembly 480 can include a pawl-like element 482 that extends through a through hole 484 of the outer sleeve 468 of the second handle 406 and abuts a tapered portion 486 of the inner sleeve 466. The tapered portion 486 includes a proximal end 486p and a distal end 486d in which the proximal end 486p forms teeth 488 extending radially outward from the inner sleeve 466. When the surgical instrument 400 is in the disengaged position, the pawl-like element 482 abuts the distal end 486d of the tapered portion 486, and therefore is not engaged. When the surgical instrument 400 is moved to its engaged position, however, the pawl-like element 482 slides along the tapered portion 486 in a proximal direction (e.g., a direction towards the proximal end 486p) and engages the teeth 488. As such, the inner sleeve 466 can only freely rotate relative to the outer sleeve 468 in a first direction that corresponds to the direction in which the first handle (not shown) rotates to bone anchor assembly into bone. When the first handle is rotated in the opposite direction, e.g., a second direction, the engagement of the pawl-like element 482 against the teeth 488 causes the inner and outer sleeves 466, 468 to rotate together. As the inner and outer sleeves 466, 468 begin to the rotate in tandem, the stylet (not shown) will begin to distally advance, thereby disengaging the ratchet assembly 480 while reengaging the first locking mechanism.

Figure 7A:
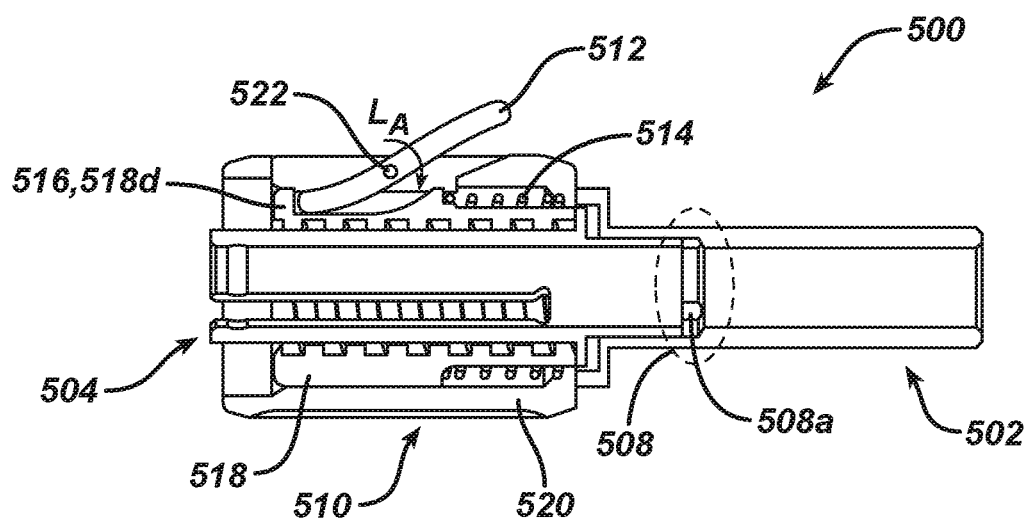
FIG. 7A is a partial, cross-sectional side view of another embodiment of a surgical instrument having a lever coupled to a distal handle and a clutch assembly, showing the surgical instrument in a disengaged position.
Figure 7B:
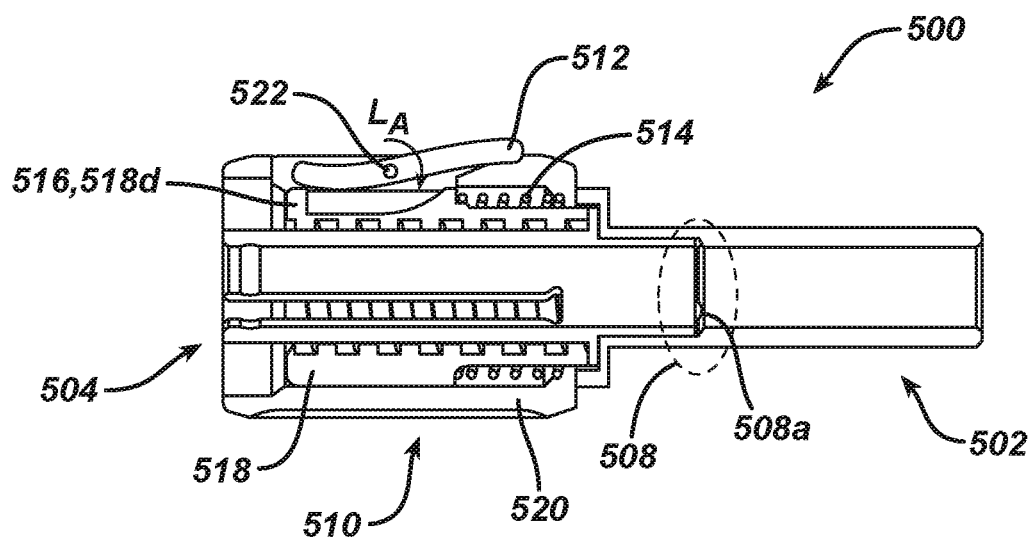
FIG. 7B is a cross-sectional view of the surgical instrument of FIG. 7A, showing the surgical instrument in an engaged position.
Figure 7C:
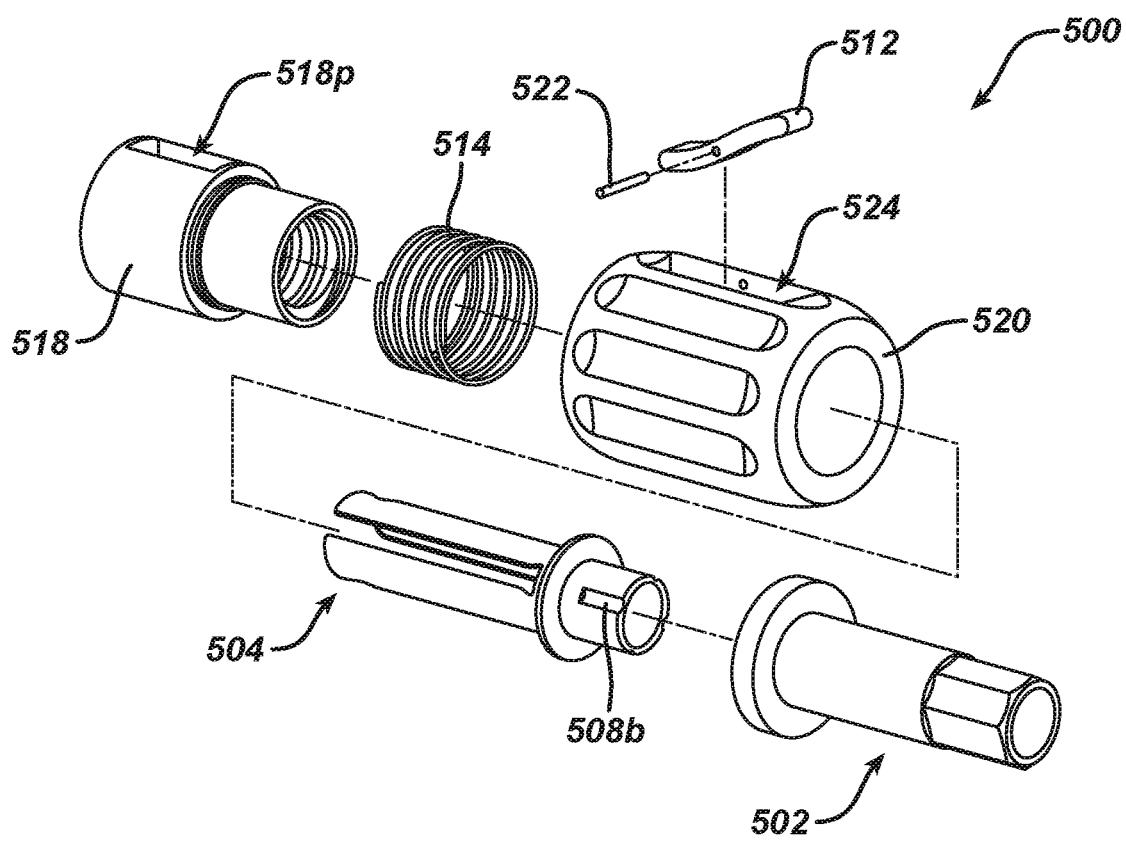
FIG. 7C is an exploded view of the surgical instrument of FIG. 7A.

FIGS. 7A-7C illustrate another exemplary embodiment of a surgical instrument for driving a bone anchor assembly into bone. Aside from the differences described in detail below, the surgical instrument 500 can be similar to surgical instrument 100 (FIGS. 1A-2E) and is therefore not described in detail herein. Further, for purposes of simplicity, certain components of the surgical instrument 500 are not illustrated in FIG. 7A-7C.

As shown, the surgical instrument 500 includes a drive tube assembly having a proximal driving tube 502 and a distal driving tube 504. While the proximal and distal driving tubes 502, 504 are prevented from axial decoupling via a locking mechanism, e.g., like the locking mechanism shown in FIGS. 8A-8C, the proximal and distal driving tubes 502, 504 rotate independently of each other when the surgical instrument 500 is in the disengaged position (i.e., the home position). FIG. 7A shows the surgical instrument 500 in its disengaged position. As a result, the first handle (not shown) is decoupled from the elongate shaft (not shown), and therefore any rotation of the first handle, when the surgical instrument 500 is in the disengaged position, is ineffective to drive a bone anchor assembly (not shown) that is attached to the elongate shaft into bone. When the surgical instrument 500 is in the engaged position (FIG. 7B), however, a clutch mechanism is engaged that couples the proximal and distal driving tubes 502, 504 together in a manner that allows the tubes 502, 504, and thus the first handle and elongate shaft, to rotate together.

The clutch mechanism, as shown in FIGS. 7A-7C, includes a clutch assembly 508 that is engaged when the second handle, also referred to as a distal handle, 510 is moved in a distal direction relative to the elongate shaft. In this exemplary embodiment, a lever 512 and a spring 514 are used to axially bias the second handle 510 in a first position (home position), when the surgical instrument 500 is in the disengaged position (FIG. 7A). In particular, the lever 512 engages with an engagement feature 516 of the inner sleeve 518 to prevent distal movement of the second handle 510. In this exemplary embodiment, the engagement feature 516 is a flange. A portion 518p of the inner sleeve 518 is removed to form the flange at the distal end 518d thereof, and the lever 512 is coupled to the outer sleeve 520 via a pin 522. The lever 512 is pivotable between a first position (FIG. 7A) and a second position (FIG. 7B).

As shown in FIG. 7A, when the lever 512 is in its first position, a distal end 512d of the lever 512 engages with the flange of the inner sleeve 518, this maintains the second handle 510 in its first position. To move the second handle 510 from its first position to a second position, and consequently, the surgical instrument 500 from its disengaged position to its engaged position, (e.g., a grasping force) a force is applied to the lever 512. The applied force causes the lever 512 to pivot about pin 522, which defines the lever pivot axis (LA), and move from its first position to its second position. When the lever 512 pivots from its first position to its second position, the lever 512 disengages from the inner sleeve 518 and moves into a substantially longitudinal position within a housing 524 in the outer sleeve 520. When the lever 512 moves into its second position, the second handle 510 can then be advanced in a distal direction such that the surgical instrument 500 can move from its disengaged position to its engaged position.

In this exemplary embodiment, the clutch assembly 508 includes a male engagement feature 508a and a female engagement feature 508b. As shown in FIGS. 7A-7C, the male engagement feature 508a is formed in the proximal driving tube 502 and the female engagement feature 508b is formed in the distal driving tube 504. When the second handle 510 is moved from its first position (FIG. 7A) to its second position (FIG. 7C), the male engagement feature 508a engages with the female engagement feature 508b, thereby coupling the proximal driving tube 502 to the distal driving tube 504. Once the male and female engagement features 508a, 508b are engaged, the surgical instrument 500 is in its engaged position. When in the engaged position, the surgical instrument 500 operates similarly to surgical instrument 100 and therefore is not described in detail herein.

Figure 8C:
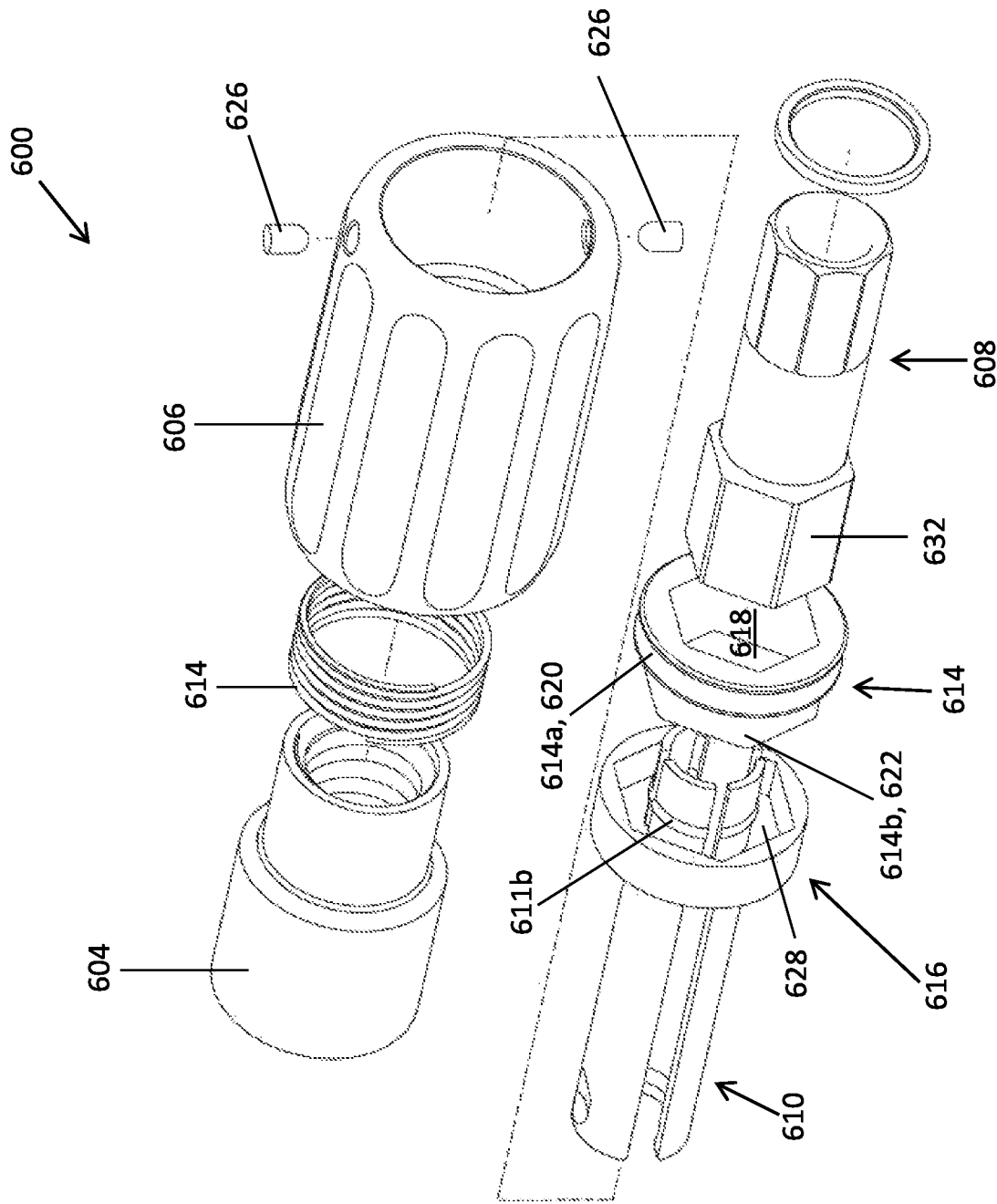
FIG. 8C is an exploded view of the surgical instrument of FIG. 8A.

FIGS. 8A-8C illustrate another exemplary embodiment of a surgical instrument for driving a bone anchor assembly into bone. Aside from the differences described in detail below, the surgical instrument 600 can be similar to surgical instrument 100 (FIGS. 1A-2E) and is therefore not described in detail herein. Further, for purposes of simplicity, certain components of the surgical instrument 600 are not illustrated in FIG. 8A-8C.

In this exemplary embodiment, the surgical instrument 600 includes a second handle 602 having an inner and outer sleeve 604, 606, and a drive tube assembly having a proximal driving tube 608 and a distal driving tube 610. The proximal and distal driving tubes 608, 610 are prevented from axial decoupling via a locking mechanism that includes male and female engagement features 611a, 611b. While the locking mechanism prevents axial decoupling of the proximal and distal driving tubes 608, 610, the tubes 608, 610 rotate independently of each other when the surgical instrument 600 is in the disengaged position (i.e., the home position). As a result, the first handle (not shown) is decoupled from the elongate shaft (not shown). FIG. 8A shows the surgical instrument 600 in its disengaged position. When the surgical instrument 600 is in the engaged position (FIG. 8B), however, a clutch mechanism is engaged that rotatably couples the proximal and distal driving tubes 608, 610 together in a manner that allows the tubes 608, 610, and thus the first handle and elongate shaft, to rotate together to facilitate driving a bone anchor assembly that is attached to the elongate shaft into bone.

As shown, the clutch mechanism includes a clutch assembly 612 having male and female engagement features 614, 616. The male engagement feature 614 includes a first portion 614a and a second portion 614b with an inner lumen 618 extending therethrough. While the first and second portions 614a, 614b can have a variety of configurations, in this exemplary embodiment, the first portion 614a has an annular outer surface 620, whereas the second portion 614b has a hexagonal outer surface 622. The annular outer surface 620 includes a recessed channel 624 that is configured to receive spring pins 626 to thereby couple the male engagement feature 614 to the outer sleeve 606 of the second handle 602. While the inner lumen 618 can have a variety of shapes, in this exemplary embodiment, the inner lumen 618 is hexagonally shaped. It is also contemplated that the inner lumen 618 and the outer surfaces 620, 622 can have other suitable shapes such as a circle or other polygonal shapes, for example, but not limited to, a square, a triangle, a rectangle, an octagon, or a dodecagon.

The female engagement feature 616, as shown in FIGS. 8A-8C, is positioned about the distal driving tube 610 and includes an internal cavity 628. When the surgical instrument 600 is in the disengaged position (FIG. 8A), the female engagement feature 616 engages with flange 630 that extends from the inner surface of the outer sleeve 606. While the internal cavity 628 can have a variety of shapes, in this exemplary embodiment, the internal cavity 628 is hexagonally shaped. It is also contemplated that the internal cavity 628 can have other suitable shapes such as a circle or other polygonal shapes, for example, but not limited to, a square, a triangle, a rectangle, an octagon, or a dodecagon.

Further, the proximal driving tube 608 includes a casing 632 about a proximal end 608p thereof. While the casing 632 can have any suitable configuration, in this exemplary embodiment, the casing 632 is hexagonally shaped. As shown, the hexagonal casing 632 is configured to engage the inner lumen 618 of the male engagement feature 614 to thereby couple the proximal driving tube 608 to the male engagement feature 614. It is this engagement, the engagement of the female engagement feature 616 and the flange 630, and the spring pins 626 that couple the outer sleeve 606 to the male engagement feature 614 that form the locking mechanism and thereby effect axial coupling of the proximal and distal driving tubes 608, 610 when the surgical instrument 600 is in the disengaged position.

In use, the second handle 602 is moved in a distal direction from a first position (FIG. 9A) to a second position (FIG. 8B), which in turn moves the surgical instrument 600 from its disengaged position to its engaged position. When the second handle 602 is moved in a distal direction, the second portion 614b of the male engagement feature 614 engages the internal cavity 628 of the female engagement feature 616, thereby rotatably coupling the proximal and distal driving tubes 608, 610. Once the male and female engagement features 614, 616 are engaged, the surgical instrument 600 is its engaged position. When the surgical instrument 600 is in its engaged position, the surgical instrument 600 operates similarly to surgical instrument 100 and therefore is not described in detail herein.

As previously mentioned, the surgical instruments can be used implant a bone anchor assembly into bone. Any suitable method can be used for operating any surgical instrument described herein. For example, when operating the surgical instrument 100 (FIGS. 1A-2E), a handle assembly that includes the proximal handle 110 and the distal handle 106 can be moved from a first configuration to a second configuration to axially translate the stylet 112. In particular, the distal handle 106 can be moved in a proximal direction relative to the proximal handle 110. Moving the handle assembly from the first configuration to the second configuration can cause the clutch mechanism to move from an disengaged position to an engaged position, and consequently, mate the proximal handle 110 to the elongate shaft 102 such that rotation of the proximal handle 110 can rotate the elongate shaft 102. In some embodiments, the handle assembly can be moved by a user manipulating the distal handle 106 (e.g., moving the distal handle in a proximal direction, or alternatively, in a distal direction). In other embodiments, the movement of the handle assembly can be automated and triggered by a specific event. The distal handle 106 can also be rotated to adjust the position of the distal tip 132 of the stylet 112 relative to the bone anchor assembly that is coupled to the distal end 102d of the elongate shaft 102. In one embodiment, the distal handle 106 can be rotated while the handle assembly is maintained in the second configuration. In another embodiment, the distal handle 106 can be rotated when the elongated shaft 102 is held stationary. Once the distal tip 132 has been adjusted to a desirable position, the surgical instrument 100 can be manipulated to insert the distal tip 132 into bone. While maintaining the handle assembly in the second configuration, once the distal tip 132 is inserted into bone, the proximal handle 110 can be rotated to rotate the elongate shaft 102 thereby distally advancing the bone anchor assembly along the stylet 112 and into bone. The rotation of the proximal handle 110 can also cause axial translation of the stylet 112 in a proximal direction relative to the elongate shaft 102. That is, rotation of the proximal handle 110, when the handle assembly is maintained in the second configuration, can effect distal advancement of the bone anchor assembly while also retracting the stylet 112.

The instruments disclosed herein can be designed to be disposed of after a single use, or they can be designed to be used multiple times. In either case, however, the instrument can be reconditioned for reuse after at least one use. Reconditioning can include any combination of the steps of disassembly of the instrument, followed by cleaning or replacement of particular pieces and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of an instrument can utilize a variety of techniques for disassembly, cleaning/replacement, and reassembly. Use of such techniques, and the resulting reconditioned instrument, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

What is claimed is:

1. An instrument for driving a bone anchor assembly into bone, comprising:
    an anchor drive assembly including a first handle and an elongate shaft having a distal tip configured to couple to a bone anchor assembly;
    a stylet assembly including a second handle and a stylet extending through the elongate shaft, the second handle having an outer sleeve and an inner sleeve; and
    a first locking mechanism that locks the outer sleeve to the inner sleeve in a first position, wherein movement of the stylet to a proximal-most position relative to the elongate shaft disengages the first locking mechanism to decouple the outer sleeve from the inner sleeve such that the inner sleeve can rotate independently of the outer sleeve;
    wherein the instrument moves from a disengaged position into an engaged position in response to axial movement of the outer sleeve relative to the inner sleeve; and
    wherein rotation of the first handle is effective to drive the bone anchor assembly into bone only when the instrument is in the engaged position, and rotation of the second handle is effective to cause axial translation of the stylet relative to the elongate shaft.

2. The instrument of claim 1, wherein the first handle is configured to be decoupled from the elongate shaft when the instrument is in the disengaged position such that the first handle is freely rotatable relative to the elongate shaft, and wherein the first handle is configured to be coupled to the elongate shaft when the instrument is in the engaged position such that rotation of the first handle rotates the elongate shaft.

3. The instrument of claim 1, wherein the stylet is configured to move proximally in response to the bone anchor assembly being driven into bone when the first handle is rotated and the instrument is in the engaged position.

4. The instrument of claim 1, wherein the stylet is configured to axially translate relative to the elongate shaft in response to rotation of the second handle while the first handle is held stationary and the instrument is in the engaged position.

5. The instrument of claim 1, further comprising a clutch mechanism having a first position and a second position, wherein the clutch mechanism in the second position is configured to couple the first handle to the elongate shaft such that rotation of the first handle rotates the elongate shaft.

6. The instrument of claim 1, further comprising a second locking mechanism that locks the outer sleeve to the inner sleeve in a second position when the first locking mechanism is disengaged, wherein distal movement of the stylet from the proximal-most position disengages the second locking mechanism and reengages the first locking mechanism such that the outer sleeve is recoupled to the inner sleeve.

7. The instrument of claim 1, wherein the stylet assembly includes a ratchet mechanism that is configured to lock the outer sleeve to the inner sleeve such that the outer and inner sleeves rotate simultaneously in one direction to distally move the stylet relative to the elongate shaft.

8. The instrument of claim 1, wherein the instrument is biased to the disengaged position.

9. The instrument of claim 1, wherein the stylet assembly includes a carrier coupled to the stylet and disposed within the anchor drive assembly and threadably coupled to the second handle.

10. A bone anchor inserter instrument, comprising:
    an elongate shaft having a distal tip configured to couple to a bone anchor assembly;
    a stylet extending through the elongate shaft; and
    a handle assembly coupled to a proximal end of the elongate shaft, the handle assembly including a first handle, a second handle, and a carrier movably disposed within the handle assembly and coupled to the stylet;
    wherein the handle assembly has a first configuration in which the first handle rotates freely relative to the elongate shaft, and a second configuration in which rotation of the first handle relative to the second handle causes corresponding rotation of the elongate shaft, and rotation of the second handle relative to the first handle causes axial translation of the carrier and the stylet coupled thereto; and
    wherein the second handle includes an outer sleeve and an inner sleeve, and wherein the inner sleeve rotates freely relative to the outer sleeve when the handle assembly is in the second configuration and the carrier is in a most-proximal position.

11. The bone anchor inserter instrument of claim 10, wherein the stylet is configured to move proximally in response to rotation of the first handle when the handle assembly is in the second configuration.

12. The bone anchor inserter instrument of claim 10, wherein the outer sleeve is configured to axially move relative to the inner sleeve to move the handle assembly from the first configuration to the second configuration.

13. The bone anchor inserter instrument of claim 10, further comprising a clutch mechanism having a first position and a second position, wherein the clutch mechanism in the second position is configured to couple the first handle to the elongate shaft such that rotation of the first handle rotates the elongate shaft.

14. The bone anchor inserter instrument of claim 10, wherein rotation of the first handle is effective to drive the bone anchor assembly into bone only when the handle assembly is in the second configuration.

15. The bone anchor inserter instrument of claim 10, wherein, when the handle assembly is in the second configuration, the carrier is non-rotatably translatable through the handle assembly in response to rotation of the second handle while the first handle is held stationary.

16. The bone anchor inserter instrument of claim 15, wherein, when the handle assembly is in the second configuration, the carrier is rotatably translatable through the handle assembly in response to rotation of the first handle while the second handle is held stationary.

* * * * *